United States Patent
Domon et al.

(10) Patent No.: US 9,604,921 B2
(45) Date of Patent: Mar. 28, 2017

(54) SULFONIUM SALT, RESIST COMPOSITION AND RESIST PATTERN FORMING PROCESS

(71) Applicant: SHIN-ETSU CHEMICAL CO., LTD., Tokyo (JP)

(72) Inventors: Daisuke Domon, Joetsu (JP); Satoshi Watanabe, Joetsu (JP); Keiichi Masunaga, Joetsu (JP); Masahiro Fukushima, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 6 days.

(21) Appl. No.: 14/861,303

(22) Filed: Sep. 22, 2015

(65) Prior Publication Data

US 2016/0090355 A1    Mar. 31, 2016

(30) Foreign Application Priority Data

Sep. 25, 2014 (JP) .................. 2014-195029

(51) Int. Cl.

| | | |
|---|---|---|
| G03F 7/039 | (2006.01) | |
| G03F 1/76 | (2012.01) | |
| G03F 7/20 | (2006.01) | |
| C07C 305/24 | (2006.01) | |
| G03F 7/004 | (2006.01) | |
| G03F 7/038 | (2006.01) | |
| G03F 7/32 | (2006.01) | |
| C07C 381/12 | (2006.01) | |
| C07D 327/08 | (2006.01) | |
| C07C 309/42 | (2006.01) | |
| C07D 333/76 | (2006.01) | |
| C07C 309/73 | (2006.01) | |
| C07D 335/12 | (2006.01) | |
| C07D 335/16 | (2006.01) | |
| C07D 339/08 | (2006.01) | |
| C07D 493/08 | (2006.01) | |
| C07D 279/20 | (2006.01) | |

(52) U.S. Cl.
CPC .......... *C07C 305/24* (2013.01); *C07C 309/42* (2013.01); *C07C 309/73* (2013.01); *C07C 381/12* (2013.01); *C07D 279/20* (2013.01); *C07D 327/08* (2013.01); *C07D 333/76* (2013.01); *C07D 335/12* (2013.01); *C07D 335/16* (2013.01); *C07D 339/08* (2013.01); *C07D 493/08* (2013.01); *G03F 1/76* (2013.01); *G03F 7/0045* (2013.01); *G03F 7/038* (2013.01); *G03F 7/039* (2013.01); *G03F 7/0382* (2013.01); *G03F 7/0392* (2013.01); *G03F 7/20* (2013.01); *G03F 7/2004* (2013.01); *G03F 7/2037* (2013.01); *G03F 7/322* (2013.01); *C07C 2101/08* (2013.01); *C07C 2101/14* (2013.01); *C07C 2101/20* (2013.01); *C07C 2103/74* (2013.01)

(58) Field of Classification Search
CPC .................................................. C07C 309/12
See application file for complete search history.

(56) References Cited

U.S. PATENT DOCUMENTS

| | | | | |
|---|---|---|---|---|
| 6,440,634 B1 * | 8/2002 | Ohsawa | ................ | C07C 309/71 430/270.1 |
| 6,692,893 B2 * | 2/2004 | Ohsawa | ................ | G03F 7/0045 430/270.1 |
| 6,861,198 B2 * | 3/2005 | Takeda | .................. | G03F 7/0382 430/270.1 |
| 7,090,961 B2 * | 8/2006 | Kobayashi | ............ | G03F 7/0395 430/270.1 |
| 7,527,912 B2 | 5/2009 | Ohsawa et al. | | |
| 7,812,105 B2 | 10/2010 | Nagai et al. | | |

(Continued)

FOREIGN PATENT DOCUMENTS

| | | |
|---|---|---|
| JP | 2004-115630 A | 4/2004 |
| JP | 2005-008766 A | 1/2005 |

(Continued)

OTHER PUBLICATIONS

English translation of JP 2009-53518, A (2009) from machine translation from AIPN Japan Patent Office National Center for Industrial Property Information and Training, generated Feb. 5, 2016, 70 pages.*

*Primary Examiner* — Cynthia Hamilton
(74) *Attorney, Agent, or Firm* — Westerman, Hattori, Daniels & Adrian, LLP

(57) ABSTRACT

A sulfonium salt of formula (0-1) is provided wherein W is alkylene or arylene, $R^{01}$ is a monovalent hydrocarbon group, m is 0, 1 or 2, k is an integer: $0 \leq k \leq 5+4m$, $R^{101}$, $R^{102}$ and $R^{103}$ are a monovalent hydrocarbon group, or at least two of $R^{101}$, $R^{102}$ and $R^{103}$ may bond together to form a ring with the sulfur atom, and L is a single bond, ester, sulfonic acid ester, carbonate or carbamate bond. A resist composition comprising the sulfonium salt as PAG exhibits a very high resolution when processed by EB and EUV lithography. A pattern with minimal LER is obtainable.

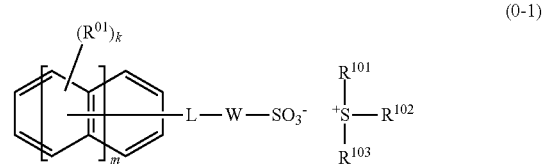

(0-1)

14 Claims, No Drawings

(56) References Cited

U.S. PATENT DOCUMENTS

| | | |
|---|---|---|
| 7,833,690 B2 * | 11/2010 | Gonsalves ............ C07C 309/29 |
| | | 430/270.1 |
| 7,897,821 B2 | 3/2011 | Nagai et al. |
| 7,977,027 B2 | 7/2011 | Takeda et al. |
| 8,343,694 B2 | 1/2013 | Koitabashi et al. |
| 8,361,693 B2 | 1/2013 | Masunaga et al. |
| 8,394,570 B2 * | 3/2013 | Ohashi ................. C07C 309/12 |
| | | 430/270.1 |
| 8,900,791 B2 | 12/2014 | Tsuchimura et al. |
| 2004/0260031 A1 | 12/2004 | Takeda et al. |
| 2011/0003251 A1 * | 1/2011 | Tanaka ................. G03F 7/0395 |
| | | 430/285.1 |

FOREIGN PATENT DOCUMENTS

| | | |
|---|---|---|
| JP | 2008-102383 A | 5/2008 |
| JP | 2008-304590 A | 12/2008 |
| JP | 2009-053518 A | 3/2009 |
| JP | 2010-100604 A | 5/2010 |
| JP | 2011-022564 A | 2/2011 |
| JP | 5083528 B2 | 11/2012 |
| WO | 2006/121096 A1 | 11/2006 |

* cited by examiner

SULFONIUM SALT, RESIST COMPOSITION AND RESIST PATTERN FORMING PROCESS

CROSS-REFERENCE TO RELATED APPLICATION

This non-provisional application claims priority under U.S.C. §119(a) on Patent Application No. 2014-195029 filed in Japan on Sep. 25, 2014, the entire contents of which are hereby incorporated by reference.

TECHNICAL FIELD

This invention relates to a sulfonium salt, a chemically amplified resist composition, and a resist pattern forming process. The chemically amplified resist composition is sensitive to high-energy radiation such as UV, deep-UV, EUV, X-ray, γ-ray, synchrotron radiation, and EB, and especially suited for use in the exposure step of irradiating high-energy radiation, typically EB or deep-UV, and adapted for microfabrication of semiconductor devices and photomask blanks.

BACKGROUND ART

To meet the recent demand for higher integration in integrated circuits, pattern formation to a finer feature size is required. Acid-catalyzed chemically amplified resist compositions are most often used in forming resist patterns with a feature size of 0.2 µm or less. High-energy radiation such as UV, deep-UV or electron beam (EB) is used as the light source for exposure of these resist compositions. In particular, while EB lithography is utilized as the ultra-fine microfabrication technique, it is also indispensable in processing a photomask blank to form a photomask for use in semiconductor device fabrication.

The resist compositions for use in photolithography include positive tone compositions wherein a pattern is formed after the exposed region is dissolved and negative tone compositions wherein the exposed region is left to form a pattern. A choice may be made depending on the desired resist pattern structure.

In general, the EB lithography is by writing an image with EB, without using a mask. In the case of positive resist, those regions of a resist film other than the regions to be retained are successively irradiated with EB having a minute area. In the case of negative resist, those regions of a resist film to be retained are successively irradiated with EB. The operation of successively scanning all finely divided regions on the work surface takes a long time as compared with full wafer exposure through a photomask. In order to avoid any decline of throughput, the resist film must be highly sensitive. Because of the long image-writing time, there is a likelihood of a difference arising between the initially written portion and the later written portion. Thus the stability with time of exposed regions in vacuum is one of important performance requirements. One of the important applications of chemically amplified resist material resides in processing of photomask blanks. Some photomask blanks have a surface material that can have an impact on the pattern profile of the overlying chemically amplified resist film, such as a layer of a chromium compound, typically chromium oxide deposited on a photomask substrate. For high resolution and profile retention after etching, it is one important performance factor to maintain the pattern profile of resist film rectangular independent of the type of substrate.

The control of resist sensitivity and pattern profile as mentioned above has been improved by a proper selection and combination of resist material-constituting components and processing conditions. One outstanding improvement is directed to the diffusion of acid that largely affects the resolution of a chemically amplified resist film. In processing of photomasks, it is required that the profile of a resist pattern formed as above do not change with a lapse of time from the end of exposure to PEB. The major cause of such a change with time is diffusion of an acid generated upon exposure. The problem of acid diffusion has been widely studied not only in the field of photomask processing, but also in the field of general resist films because it has a significant impact on sensitivity and resolution.

Patent Documents 1 and 2 describe acid generators capable of generating bulky acids for controlling acid diffusion and reducing roughness. Since these acid generators are still insufficient in control of acid diffusion, it is desired to have an acid generator with more controlled diffusion.

Patent Document 3 discloses a resist composition comprising a base resin to which a sulfonic acid generated upon light exposure is bound so that the acid diffusion is controlled. This approach of controlling acid diffusion by binding recurring units capable of generating acid upon exposure to a base polymer is effective in forming a pattern with minimal LER. However, a problem arises with respect to the solubility in organic solvent of the base polymer having bound therein recurring units capable of generating acid upon exposure, depending on the structure and proportion of such recurring units.

Polymers comprising a major proportion of aromatic structure having an acidic side chain, for example, polyhydroxystyrene have been widely used in resist materials for the KrF excimer laser lithography. These polymers are not used in resist materials for the ArF excimer laser lithography since they exhibit strong absorption at a wavelength around 200 nm. These polymers, however, are expected to form useful resist materials for the EB and EUV lithography for forming patterns of finer size than the processing limit of ArF excimer laser because they offer high etching resistance.

Often used as the base polymer in positive resist compositions for EB and EUV lithography is a polymer having an acidic functional group on phenol side chain masked with an acid labile protective group wherein the acid labile protective group is deprotected by the catalysis of an acid generated from a photoacid generator upon exposure to high-energy radiation so that the polymer may become soluble in alkaline developer. Typical of the acid labile protective group are tertiary alkyl, tert-butoxycarbonyl, and acetal groups. On use of protective groups requiring a relatively low level of activation energy for deprotection such as acetal groups, a resist film having a high sensitivity is advantageously obtainable. However, if the diffusion of generated acid is not fully controlled, deprotection reaction can occur even in the unexposed regions of the resist film, giving rise to problems like degradation of line edge roughness (LER) and a lowering of in-plane uniformity of pattern line width (CDU).

Patent Document 4 describes a resist composition comprising a resin comprising recurring units having an acetal group and a sulfonium salt capable of generating an acid having a high pKa such as fluoroalkanesulfonic acid. Regrettably, the pattern obtained therefrom has substantial LER. This is because the acid strength of fluoroalkanesulfonic acid is too high for the deprotection of an acetal group requiring a relatively low level of activation energy for deprotection. So, even if acid diffusion is controlled, deprotection reaction can occur in the unexposed region with a minor amount of acid diffused thereto.

The problem that due to acid diffusion, undesired reaction occurs in the unexposed region to incur roughness degradation is common to negative resist compositions for EB lithography and resist compositions for EUV lithography. In the case of negative resist compositions, undesirable cross-linking reaction takes place in the unexposed region due to the acid diffused thereto, and as a result, patterns with noticeable LER are formed.

CITATION LIST

Patent Document 1: JP-A 2009-053518
Patent Document 2: JP-A 2010-100604
Patent Document 3: JP-A 2011-022564
Patent Document 4: JP 5083528

DISCLOSURE OF INVENTION

An object of the invention is to provide a sulfonium salt capable of generating an acid having an appropriate strength and controlled diffusion, a resist composition, specifically chemically amplified resist composition, and a resist pattern forming process.

The inventors have found that a sulfonium salt as defined below generates a bulky acid which is controlled in diffusion, and that a pattern with minimal LER is obtainable from a resist composition comprising the sulfonium salt.

In one aspect, the invention provides a sulfonium salt having the general formula (0-1).

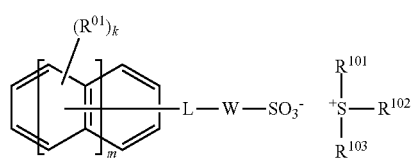

Herein W is a $C_1$-$C_{10}$ alkylene or $C_6$-$C_{18}$ arylene group which may contain an ethereal oxygen atom, $R^{01}$ is a $C_1$-$C_{10}$ straight or $C_3$-$C_{20}$ branched or cyclic monovalent hydrocarbon group which may be substituted with or separated by a heteroatom, m is an integer of 0 to 2, k is an integer satisfying $0 \leq k \leq 5+4m$, $R^{101}$, $R^{102}$ and $R^{103}$ are each independently a $C_1$-$C_{20}$ straight or $C_3$-$C_{20}$ branched or cyclic monovalent hydrocarbon group which may be substituted with or separated by a heteroatom, or at least two of $R^{101}$, $R^{102}$ and $R^{103}$ may bond together to form a ring with the sulfur atom, and L is a single bond, or an ester, sulfonic acid ester, carbonate or carbamate bond.

A sulfonium salt having the general formula (1) is preferred.

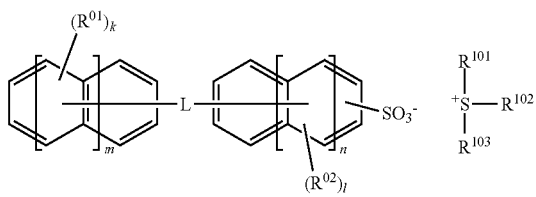

Herein $R^{01}$, m, k, $R^{101}$, $R^{102}$, $R^{103}$, and L are as defined above, $R^{02}$ is a $C_1$-$C_{10}$ straight or $C_3$-$C_{20}$ branched or cyclic monovalent hydrocarbon group which may be substituted with or separated by a heteroatom, n is an integer of 0 to 2, and l is an integer satisfying $0 \leq l \leq 4+4n$.

In another aspect, the invention provides a resist composition comprising the sulfonium salt defined above.

The resist composition may further comprise a polymer comprising recurring units having the general formula (U-1).

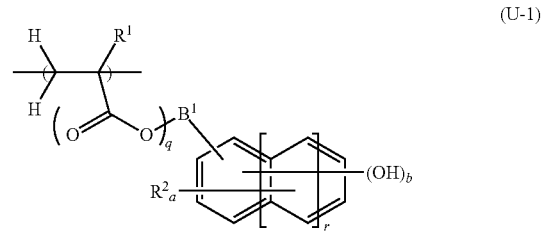

Herein q is 0 or 1, r is an integer of 0 to 2, $R^1$ is hydrogen, fluorine, methyl or trifluoromethyl, $R^2$ is each independently hydrogen or $C_1$-$C_6$ alkyl group, $B^1$ is a single bond or a $C_1$-$C_{10}$ alkylene group which may contain an ether bond, a is an integer satisfying $a \leq 5+2r-b$, and b is an integer of 1 to 3.

In one embodiment, the resist composition is a chemically amplified positive tone resist composition, the polymer comprising recurring units adapted to be decomposed under the action of acid to increase the solubility in alkaline developer.

Preferably, the recurring unit adapted to be decomposed under the action of acid to increase the solubility in alkaline developer has the general formula (U-2).

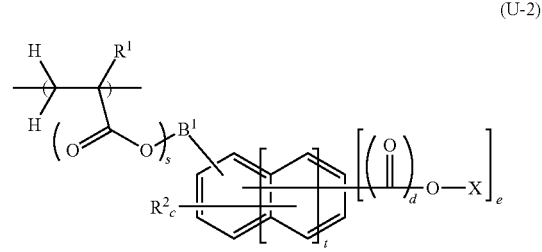

Herein s is 0 or 1, t is an integer of 0 to 2, $R^1$, $R^2$ and $B^1$ are as defined above, c is an integer satisfying $c \leq 5+2t-e$, d is 0 or 1, e is an integer of 1 to 3, X is an acid labile group when e=1, X is hydrogen or an acid labile group when e=2 or 3, with at least one Y being an acid labile group.

In another embodiment, the resist composition is a chemically amplified negative tone resist composition, the polymer comprising, in addition to the recurring units having formula (U-1), recurring units having the general formula (UN-2).

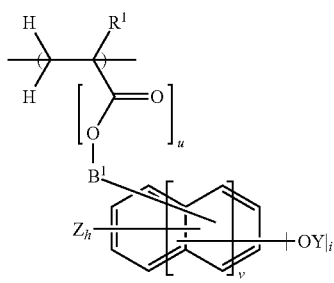
(UN-2)

Herein $R^1$ and $B^1$ are as defined above, Z is hydrogen, or a $C_1$-$C_{20}$ straight, branched or cyclic alkyl, $C_2$-$C_{20}$ hydroxyalkyl, $C_2$-$C_{20}$ alkoxyalkyl, $C_2$-$C_{20}$ alkylthioalkyl, halogen, nitro, cyano, sulfinyl, or sulfonyl group, Y is a $C_1$-$C_{20}$ alkyl or $C_1$-$C_{20}$ acyl group, h is an integer of 0 to 4, i is an integer of 0 to 5, u is 0 or 1, and v is an integer of 0 to 2.

The negative tone resist composition may further comprise a crosslinker.

In the negative tone resist composition, the polymer may further comprise recurring units having the general formula (U-3) and/or (U-4).

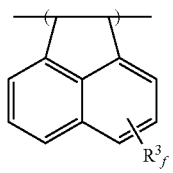
(U-3)

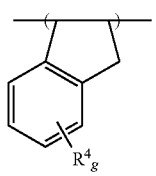
(U-4)

Herein f is an integer of 0 to 6, $R^3$ is each independently hydrogen, or a $C_1$-$C_6$ alkyl, primary or secondary alkoxy, or $C_1$-$C_7$ alkylcarbonyloxy group which may be substituted with halogen, g is an integer of 0 to 4, and $R^4$ is each independently hydrogen, or a $C_1$-$C_6$ alkyl, primary or secondary alkoxy, or $C_1$-$C_7$ alkylcarbonyloxy group which may be substituted with halogen.

The resist composition may further comprise at least one of basic compounds having the general formulae (7) to (9).

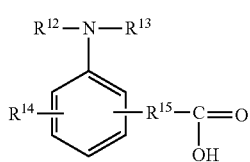
(7)

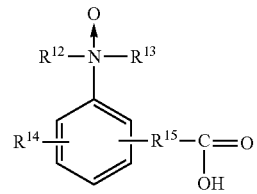
(8)

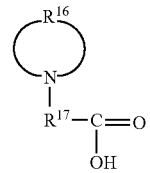
(9)

Herein $R^{12}$ and $R^{13}$ each are a $C_1$-$C_{20}$ straight, branched or cyclic alkyl, $C_6$-$C_{20}$ aryl, $C_7$-$C_{20}$ aralkyl, $C_2$-$C_{20}$ hydroxyalkyl, $C_2$-$C_{20}$ alkoxyalkyl, $C_2$-$C_{20}$ acyloxyalkyl, or $C_2$-$C_{20}$ alkylthioalkyl group, or $R^{12}$ and $R^{13}$ may bond together to form a cyclic structure with the nitrogen atom to which they are attached, $R^{14}$ is hydrogen, a $C_1$-$C_{20}$ straight, branched or cyclic alkyl, $C_6$-$C_{20}$ aryl, $C_7$-$C_{20}$ aralkyl, $C_2$-$C_{20}$ hydroxyalkyl, $C_2$-$C_{20}$ alkoxyalkyl, $C_2$-$C_{20}$ acyloxyalkyl, or $C_2$-$C_{20}$ alkylthioalkyl group, or halogen, $R^{15}$ is a single bond, a $C_1$-$C_{20}$ straight, branched or cyclic alkylene or $C_6$-$C_{20}$ arylene group, $R^{16}$ is an optionally substituted, $C_1$-$C_{20}$ straight or branched alkylene group which may contain at least one carbonyl, ether, ester or sulfide bond between two carbon atoms thereof, and $R^{17}$ is a $C_1$-$C_{20}$ straight, branched or cyclic alkylene or $C_6$-$C_{20}$ arylene group.

In a further aspect, the invention provides a pattern forming process comprising the steps of applying the resist composition defined above onto a processable substrate to form a resist film, exposing patternwise the resist film to high-energy radiation, and developing in an alkaline developer to form a resist pattern.

The high-energy radiation is typically EUV or EB. The processable substrate may have an outermost surface made of a chromium-containing material. Typically, the processable substrate is a photomask blank.

Advantageous Effects of Invention

A resist composition comprising the sulfonium salt defined herein as PAG exhibits a very high resolution when processed by the micropatterning lithography, especially EB and EUV lithography. A pattern with minimal LER is obtainable therefrom.

DESCRIPTION OF PREFERRED EMBODIMENTS

As used herein, the singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group. The term "film" is used interchangeably with "coating" or "layer." The term "processable layer" is interchangeable with patternable layer and refers to a layer that can be processed such as by etching to form a pattern therein.

The abbreviations and acronyms have the following meaning.
PAG: photoacid generator
Mw: weight average molecular weight
Mn: number average molecular weight
Mw/Mn: molecular weight distribution or dispersity
GPC: gel permeation chromatography
PEB: post-exposure baking
PED: post-exposure delay
LER: line edge roughness
CDU: critical dimension uniformity It is understood that for some structures represented by chemical formulae, there can exist enantiomers and diastereomers because of the presence of asymmetric carbon atoms. In such a case, a single formula collectively represents all such isomers. The isomers may be used alone or in admixture. In chemical formulae, the broken line denotes a valence bond.

Sulfonium Salt

One embodiment of the invention is a sulfonium salt having the general formula (0-1).

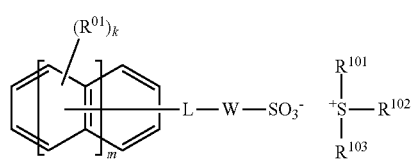
(0-1)

Herein W is a $C_1$-$C_{10}$ alkylene or $C_6$-$C_{18}$ arylene group which may contain an ethereal oxygen atom. $R^{01}$ is a $C_1$-$C_{10}$ straight or $C_3$-$C_{20}$ branched or cyclic monovalent hydrocarbon group which may be substituted with or separated by a heteroatom, m is an integer of 0 to 2, and k is an integer satisfying $0 \le k \le 5+4m$. $R^{101}$, $R^{102}$ and $R^{103}$ are each independently a $C_1$-$C_{20}$ straight or $C_3$-$C_{20}$ branched or cyclic monovalent hydrocarbon group which may be substituted with or separated by a heteroatom, or at least two of $R^{101}$, $R^{102}$ and $R^{103}$ may bond together to form a ring with the sulfur atom. L is a single bond, or an ester, sulfonic acid ester, carbonate or carbamate bond.

The preferred form of the onium salt having formula (0-1) is an onium salt having the general formula (1).

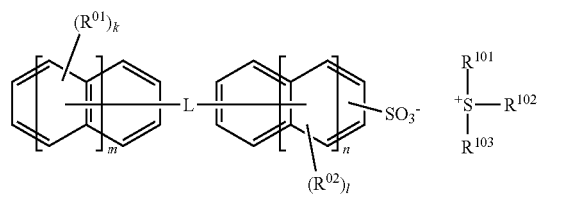
(I)

Herein $R^{01}$, m, k, $R^{101}$, $R^{102}$, $R^{103}$, and L are as defined above, $R^{02}$ is a $C_1$-$C_{10}$ straight or $C_3$-$C_{20}$ branched or cyclic monovalent hydrocarbon group which may be substituted with or separated by a heteroatom, n is an integer of 0 to 2, and l is an integer satisfying $0 \le l \le 4+4n$.

In formulae (0-1) and (1), $R^{01}$ and $R^{02}$ are each independently a $C_1$-$C_{10}$ straight or $C_3$-$C_{20}$ branched or cyclic monovalent hydrocarbon group which may be substituted with or separated by a heteroatom. Examples of the hydrocarbon group include, but are not limited to, methyl, ethyl, propyl, isopropyl, n-butyl, sec-butyl, tert-butyl, methoxy, ethoxy, propoxy, isopropoxy, butoxy, tert-amyl, n-pentyl, n-hexyl, n-octyl, n-nonyl, n-decyl, pentyloxy, hexyloxy, cyclopentyl, cyclohexyl, cyclopentyloxy, cyclohexyloxy, 2-ethylhexyl, cyclopentylmethyl, cyclopentylethyl, cyclopentylbutyl, cyclohexylmethyl, cyclohexylethyl, cyclohexylbutyl, norbornyl, oxanorbornyl, tricyclo[$5.2.1.0^{2,6}$]decanyl, and adamantyl.

Preferably $R^{02}$ is positioned at ortho-position relative to the $SO_3^-$ group. This is because the $SO_3^-$ group which is an acid-working moiety is shielded by steric bulkiness, leading to an effect of apparently suppressing acid diffusion.

In formulae (0-1) and (1), L is a single bond, or an ester, sulfonic acid ester, carbonate or carbamate bond.

In formulae (0-1) and (1), m is an integer of 0 to 2, and k is an integer satisfying $0 \le k \le 5+4m$. From the standpoint of controlling dissolution during development, m is preferably 0 or 1, most preferably 0. It is preferred from the standpoint of introducing a substituent into the salt to impart appropriate bulkiness to the acid generated upon exposure that k be an integer of 0 to 5, more preferably 1 to 3.

In formulae (0-1) and (1), n is an integer of 0 to 2, and l is an integer satisfying $0 \le l \le 4+4n$. Preferably, n is 0 or 1, most preferably 0. It is preferred from the standpoint of introducing a substituent into the salt to control the diffusion of the acid generated upon exposure that l be an integer of 0 to 4, more preferably 2 or 3.

In formula (0-1), W is a $C_1$-$C_{10}$ alkylene or $C_6$-$C_{18}$ arylene group which may contain an ethereal oxygen atom. Examples of the alkylene and arylene groups are shown below, but not limited thereto.

(W-1)

(W-2)

(W-3)

(W-4)

(W-5)

(W-6)

(W-7)

(W-8) 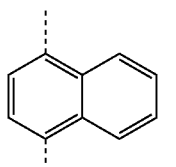
(W-9) 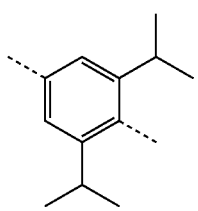
(W-10) 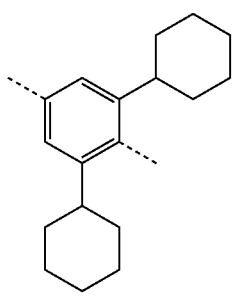
(W-11) 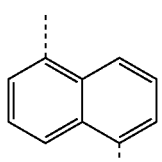
(W-12) 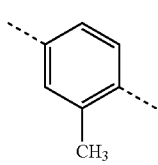
(W-13) 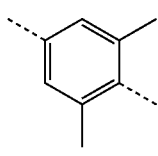
(W-14) 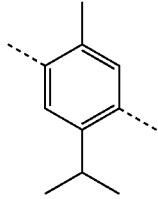
(W-15) 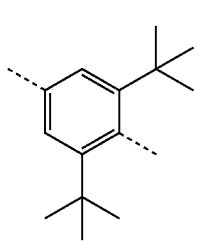
(W-16) 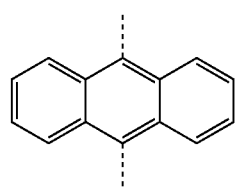
In the above formulae, two broken lines denote valence bonds, which bond with L and $SO_3^-$ group in formula (0-1). When either one of the valence bonds bonds with L, the other bonds with $SO_3^-$ group.
In formulae (0-1) and (1), examples of the aromatic ring structure to which $R^{01}$ and L are attached are shown below, but not limited thereto.
(B-1) 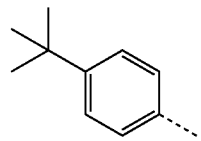
(B-2) 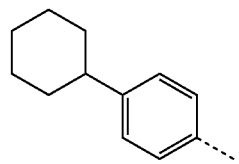
(B-3) 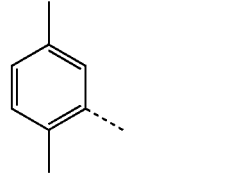
(B-4) 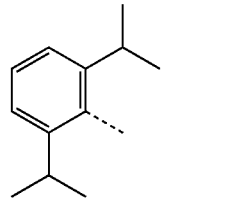
(B-5) 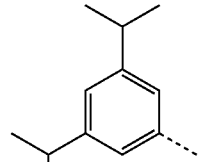
(B-6) 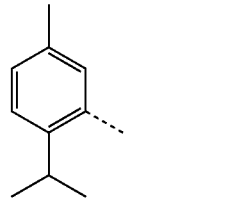

(B-7)
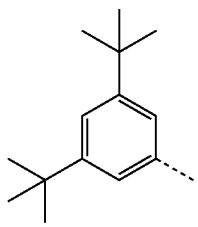

(B-8)
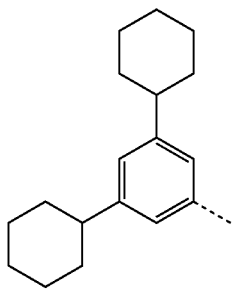

(B-9)
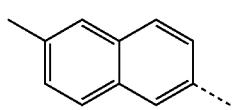

(B-10)
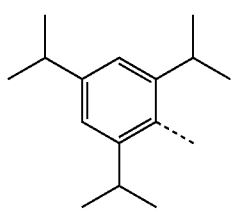

(B-11)
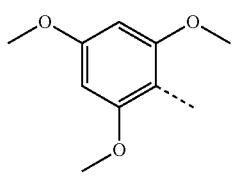

(B-12)
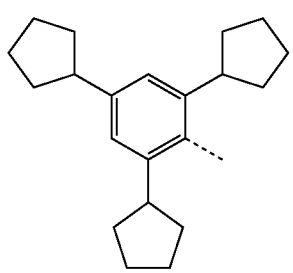

(B-13)
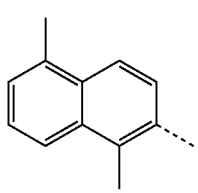

(B-14)
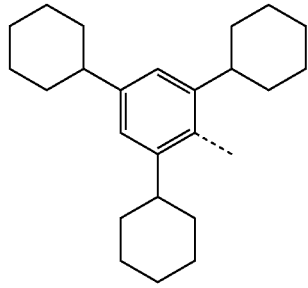

(B-15)
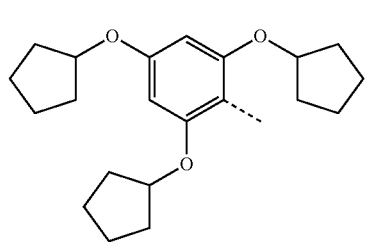

(B-16)
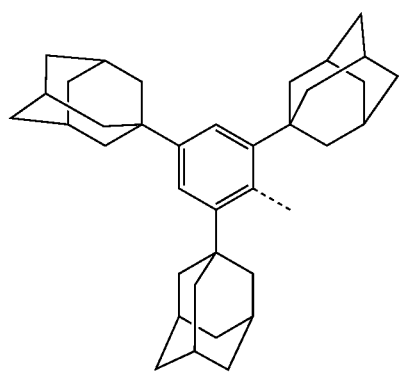

In the above formulae, the broken line denotes a valence bond with L.

Preferred structures for the anion moiety in the sulfonium salt of formula (0-1) or (1) include those structures obtained from an arbitrary combination of the following three:

(a) any of units (W-1) to (W-16),
(b) any of units (B-1) to (B-16), and
(c) a bond mode represented by L.

More preferred structures for the anion moiety in the sulfonium salt of formula (0-1) or (1) are exemplified below, but not limited thereto.

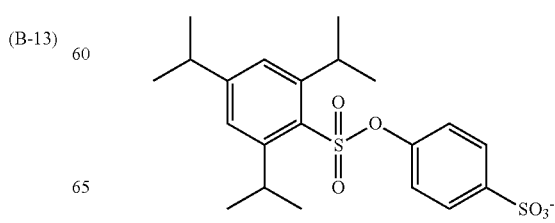

-continued
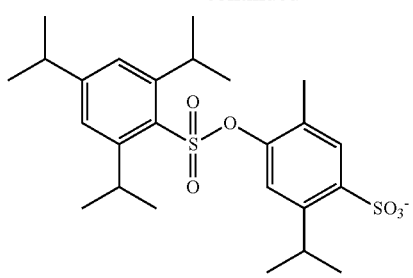
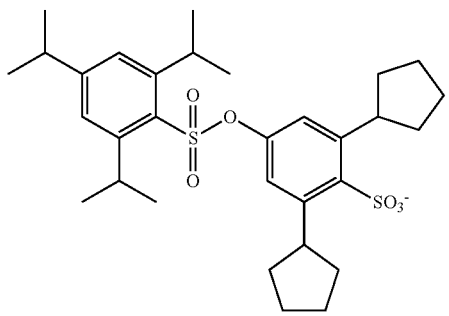
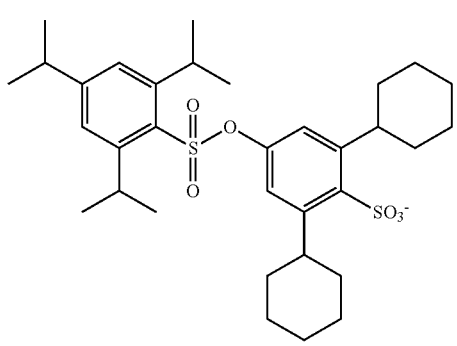
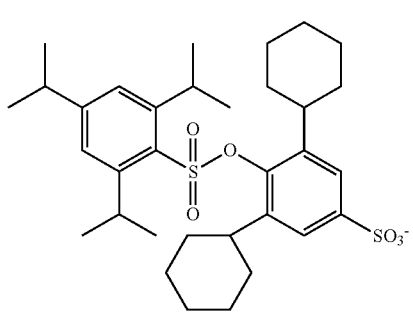
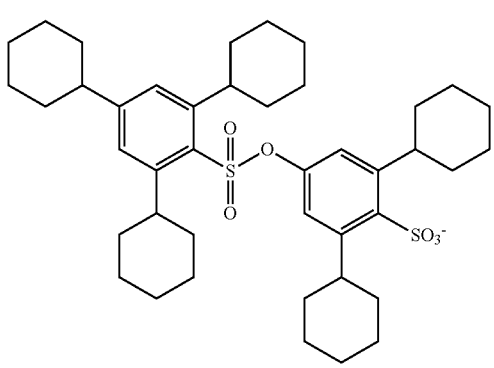
-continued
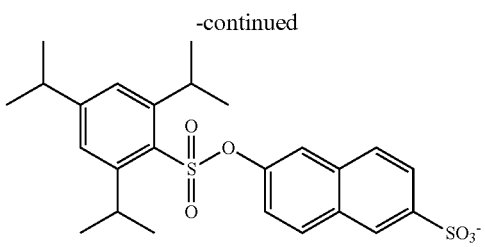
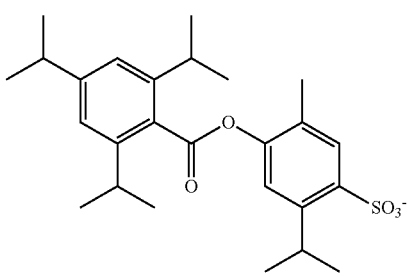
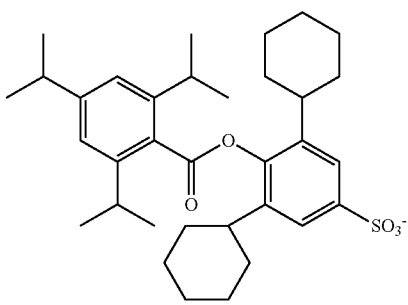
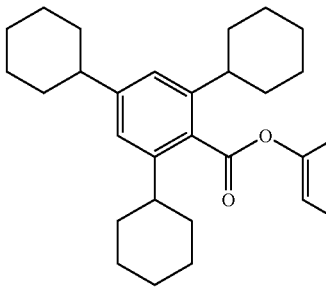
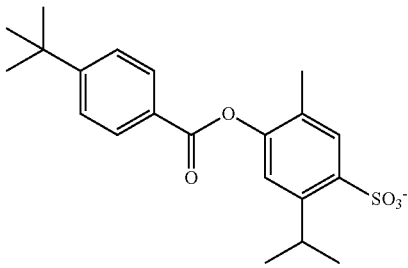
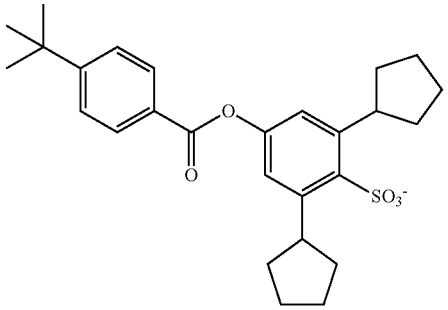

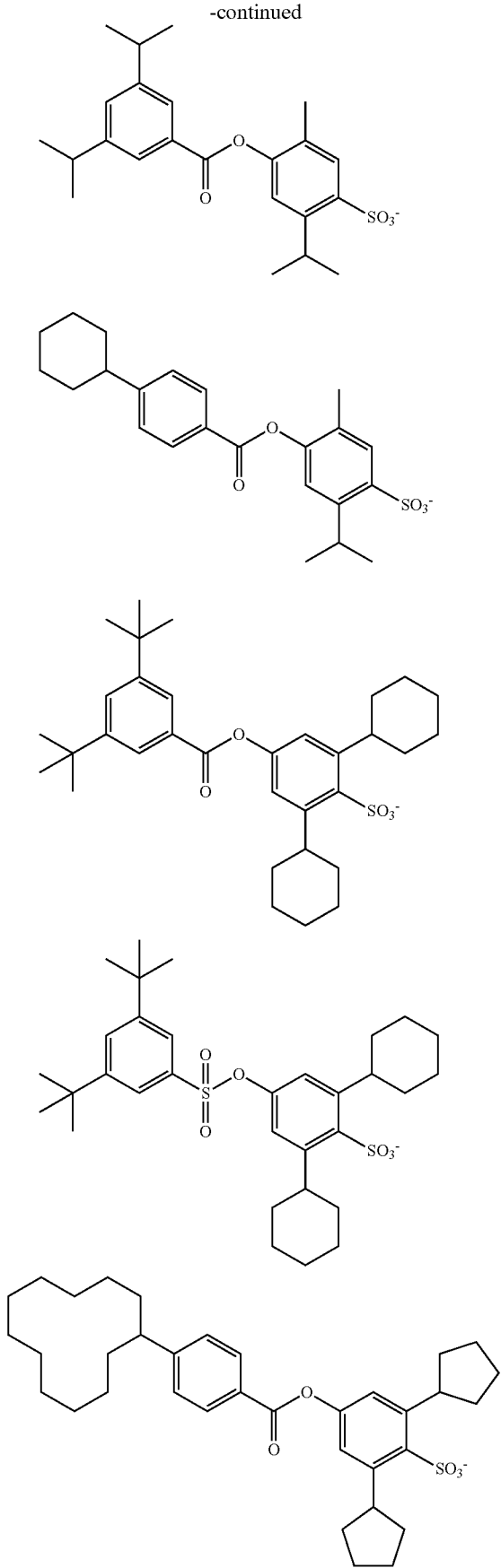

-continued

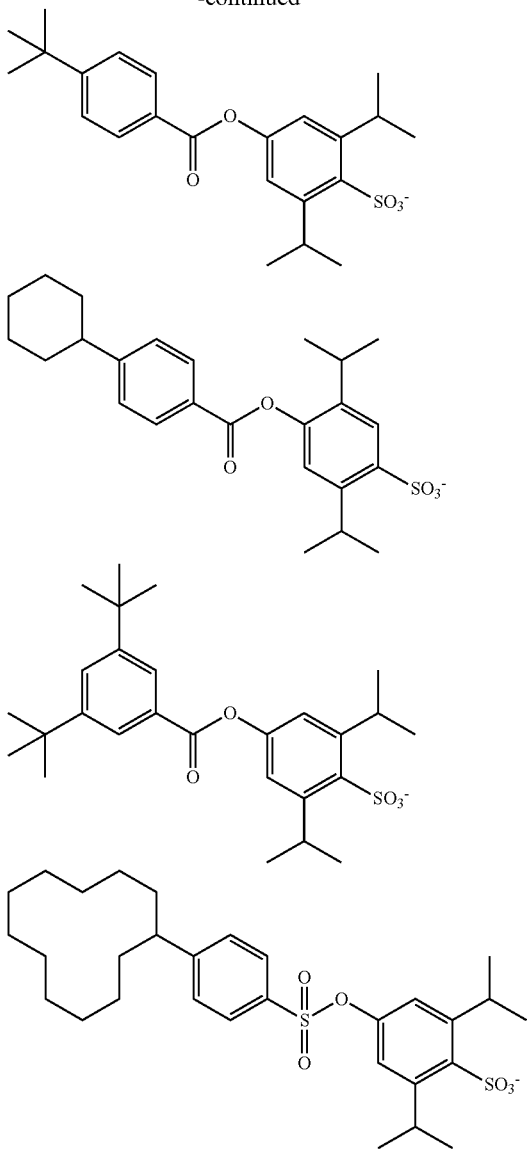

In formulae (0-1) and (1), $R^{101}$, $R^{102}$ and $R^{103}$ are each independently a $C_1$-$C_{20}$ straight or $C_3$-$C_{20}$ branched or cyclic monovalent hydrocarbon group which may be substituted with or separated by a heteroatom, or at least two of $R^{101}$, $R^{102}$ and $R^{103}$ may bond together to form a ring with the sulfur atom in the formula.

Suitable hydrocarbon groups include alkyl groups such as methyl, ethyl, n-propyl, isopropyl, n-butyl, tert-butyl, cyclopropyl, cyclopentyl, cyclohexyl, cyclopropylmethyl, 4-methylcyclohexyl, cyclohexylmethyl, norbornyl, and adamantyl; alkenyl groups such as vinyl, allyl, propenyl, butenyl, hexenyl, and cyclohexenyl; aryl groups such as phenyl, naphthyl and thienyl; and aralkyl groups such as benzyl, 1-phenylethyl, and 2-phenylethyl. Inter alia, aryl groups are preferred. Also included are substituted forms of the foregoing in which one or more hydrogen is substituted by a heteroatom such as oxygen, sulfur, nitrogen or halogen, or which is separated by a heteroatom such as oxygen, sulfur or nitrogen, so that a hydroxyl group, cyano group, carbonyl group, ether bond, ester bond, sulfonic acid ester bond, carbonate bond, lactone ring, sultone ring, carboxylic anhydride, or haloalkyl group forms or intervenes.

Alternatively, any two of $R^{101}$, $R^{102}$ and $R^{103}$ may bond together to form a ring with the sulfur atom in the formula. Exemplary ring structure-forming groups are shown below.

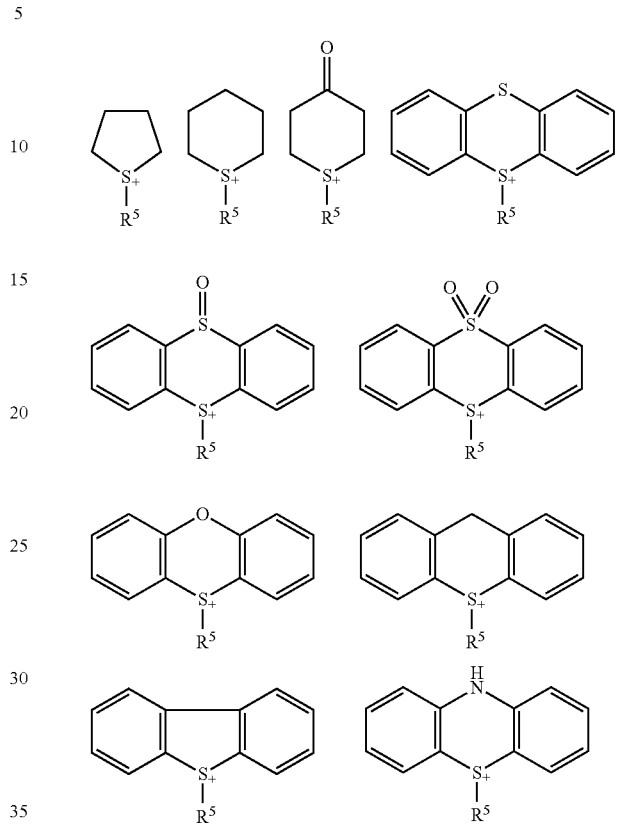

Herein $R^5$ is as defined and exemplified above for $R^{101}$, $R^{102}$ and $R^{103}$.

Preferred structures for the cation moiety in the sulfonium salt of formula (0-1) or (1) are exemplified below, but not limited thereto.

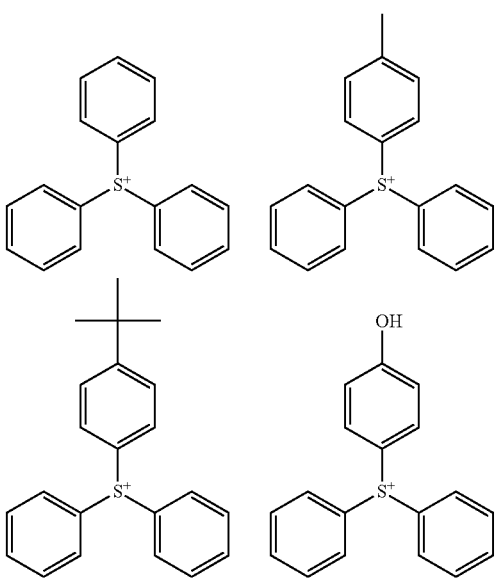

-continued

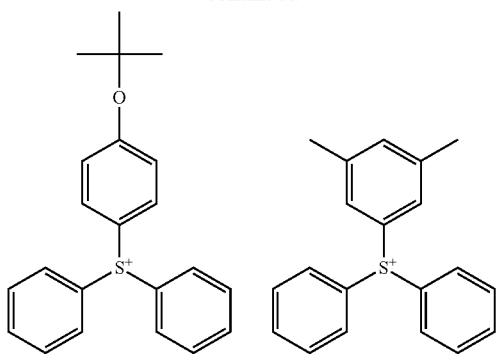
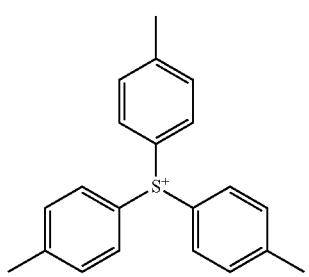
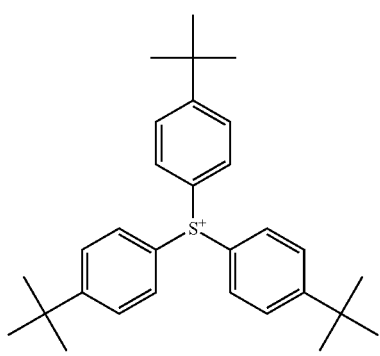
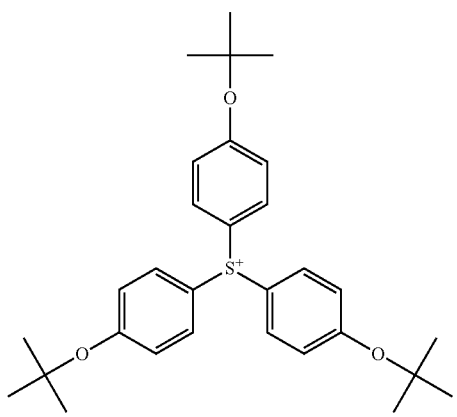
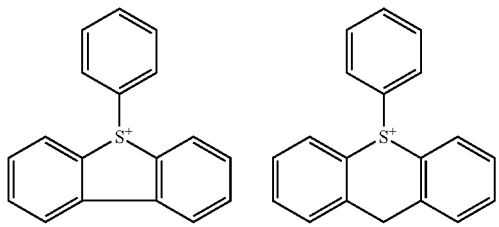

-continued

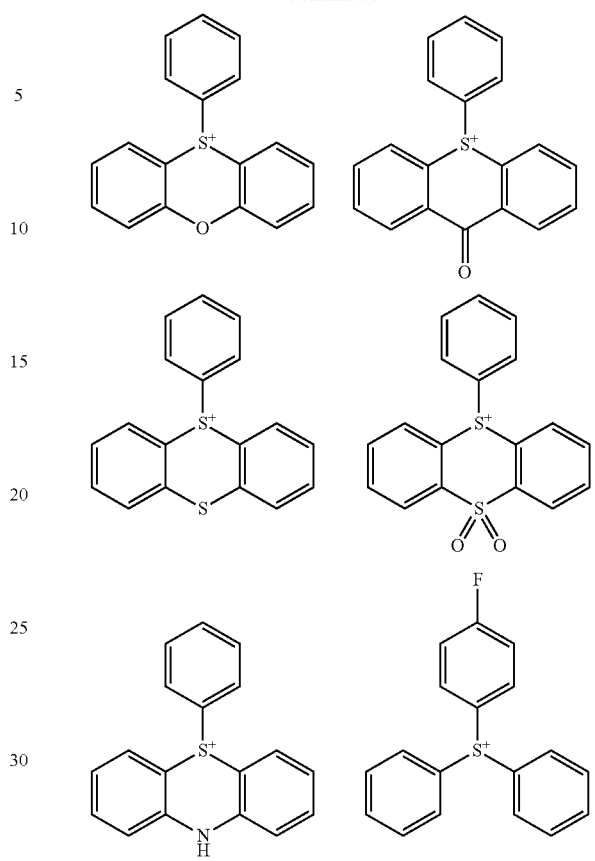

Exemplary structure of the sulfonium salt include arbitrary combinations of the above-exemplified anions with the above-exemplified cations.

The method for preparing the sulfonium salt having formula (1), for example, formula (1) wherein L is an ester bond or sulfonic acid ester bond is exemplified by the following reaction scheme, but not limited thereto.

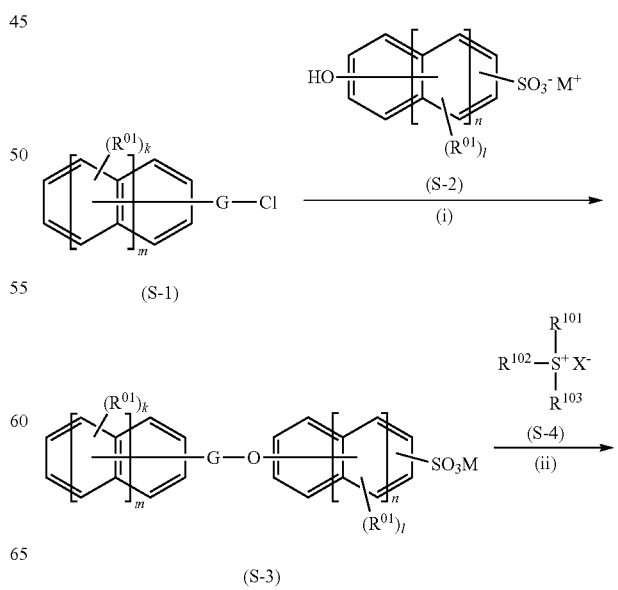

-continued

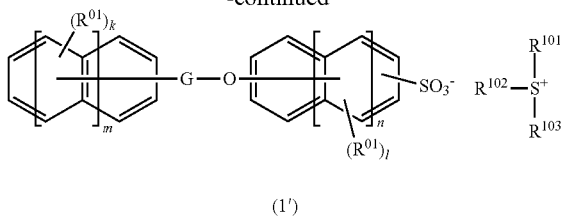

(1')

Herein $R^{01}$, $R^{02}$, m, n, k, l, $R^{101}$, $R^{102}$ and $R^{103}$ are as defined above, G is a carbonyl or sulfonyl group, $M^+$ is a lithium ion, sodium ion, potassium ion or substituted or unsubstituted ammonium ion, and $X^-$ is a halide ion or methylsulfate ion.

Step (i) is nucleophilic displacement reaction of acid chloride (S-1) with hydroxyarylsulfonic acid salt (S-2) to form sulfonic acid salt (S-3). The reaction may be conducted by the standard technique, specifically by sequentially or simultaneously adding the acid chloride (S-1), the hydroxyarylsulfonic acid salt (S-2), and a base to a solvent and allowing the reaction to take place while cooling or heating if necessary.

Suitable solvents which can be used in step (i) include water; ethers such as tetrahydrofuran, diethyl ether, diisopropyl ether, di-n-butyl ether and 1,4-dioxane; hydrocarbons such as n-hexane, n-heptane, benzene, toluene, and xylene; aprotic polar solvents such as acetonitrile, dimethyl sulfoxide (DMSO) and N,N-dimethylformamide (DMF); and chlorinated solvents such as methylene chloride, chloroform and carbon tetrachloride. The solvent may be selected depending on reaction conditions while it may be used alone or in admixture.

Suitable bases which can be used in step (i) include amines such as ammonia, triethylamine, pyridine, lutidine, collidine, and N,N-dimethylaniline; hydroxides such as sodium hydroxide, potassium hydroxide and tetramethylammonium hydroxide; and carbonates such as potassium carbonate and sodium hydrogencarbonate, which may be used alone or in admixture.

Step (ii) is ion exchange reaction between sulfonic acid salt (S-3) and sulfonium salt (S-4) to form sulfonium salt (1'). As the sulfonic acid salt (S-3), the reaction product resulting from step (i) may be used in crude form or after it is isolated by customary aqueous work-up.

Where the isolated form of sulfonic acid salt (S-3) is used, a reaction mixture is obtained by dissolving the salt in a solvent, mixing with sulfonium salt (S-4), and optionally cooling or heating. Examples of the solvent used herein include water; ethers such as tetrahydrofuran, diethyl ether, diisopropyl ether, di-n-butyl ether and 1,4-dioxane; hydrocarbons such as n-hexane, n-heptane, benzene, toluene, and xylene; aprotic polar solvents such as acetonitrile, dimethyl sulfoxide (DMSO) and N,N-dimethylformamide (DMF); and chlorinated solvents such as methylene chloride, chloroform and carbon tetrachloride. From the reaction mixture, sulfonium salt (1') may be recovered via customary aqueous work-up. If necessary, the salt may be purified by standard techniques like distillation, recrystallization and chromatography.

Where the crude form of sulfonic acid salt (S-3) is used, a sulfonium salt (1') is obtained by adding sulfonium salt (S-4) to the reaction mixture at the end of synthesis reaction (step i) of sulfonic acid salt (S-3) and optionally cooling or heating. If necessary, a solvent may be added to the reaction mixture. Examples of the solvent include water; ethers such as tetrahydrofuran, diethyl ether, diisopropyl ether, di-n-butyl ether and 1,4-dioxane; hydrocarbons such as n-hexane, n-heptane, benzene, toluene, and xylene; aprotic polar solvents such as acetonitrile, dimethyl sulfoxide (DMSO) and N,N-dimethylformamide (DMF); and chlorinated solvents such as methylene chloride, chloroform and carbon tetrachloride. From the reaction mixture, sulfonium salt (1') may be recovered via customary aqueous work-up. If necessary, the salt may be purified by standard techniques like distillation, recrystallization and chromatography.

Since the sulfonium salt of formula (1) according to the invention has a sulfonium salt structure of non-fluorinated sulfonic acid, it generates an acid with appropriate strength upon exposure to high-energy radiation. Since the sulfonium salt has a bulky substituent group, the movement and diffusion of the generated acid can be appropriately controlled, contributing to roughness improvement. Since the sulfonium salt is fully lipophilic, it is easy to prepare and handle.

Understandably, any corresponding onium salts such as iodonium and ammonium salts may be synthesized by the same method as the synthesis of the sulfonium salt having formula (1). These onium salts may be equally applicable to chemically amplified resist compositions.

Examples of the iodonium cation include diphenyliodonium, bis(4-methylphenyl)iodonium, bis(4-(1,1-dimethylethyl)phenyl)iodonium, bis(4-(1,1-dimethylpropyl)phenyl)iodonium, and (4-(1,1-dimethylethoxy)phenyl)phenyliodonium. Examples of the ammonium cation include tertiary ammonium cations such as trimethylammonium, triethylammonium, tributylammonium, and N,N-dimethylanilinium, and quaternary ammonium cations such as tetramethylammonium, tetraethylammonium, and tetrabutylammonium. These iodonium and ammonium salts may be used as exerting a photoacid generating effect or thermal acid generating effect.

Resist Composition

Another embodiment of the invention is a resist composition comprising a sulfonium salt having formula (0-1) or (1) capable of generating a sulfonic acid having the following formula (0-1a) or (1a) in response to high-energy radiation or heat, as an acid generator.

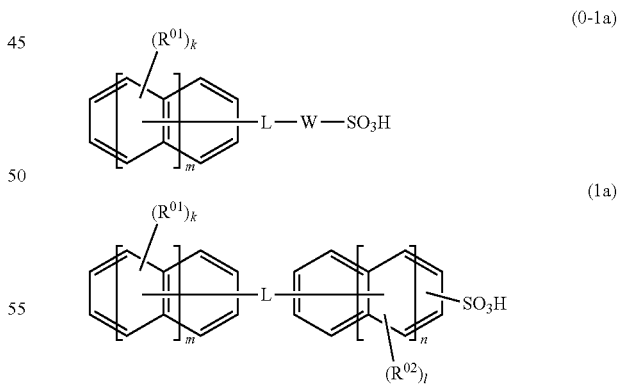

Herein W, $R^{01}$, $R^{02}$, m, n, k, l, and L are as defined above.

Typical of the resist composition is a chemically amplified resist composition comprising the acid generator defined herein, a base resin, and an organic solvent. In this embodiment, when the sulfonium salt is formulated as the acid generator, its amount is preferably 0.1 to 40 parts, more preferably 1 to 20 parts by weight per 100 parts by weight of the base resin. If the amount of sulfonium salt exceeds 40 pbw, the composition may have an excessively high sensitivity and lack shelf stability. If the amount of sulfonium salt is less than 0.1 pbw, an amount of acid generated may be insufficient to deprotect the acid labile group.

Positive Resist Composition

When a positive resist composition is prepared, a polymer adapted to be decomposed under the action of acid to increase its solubility in alkaline developer is preferably used as the base resin. Desirably the base resin is a polymer comprising recurring units having the general formula (U-1).

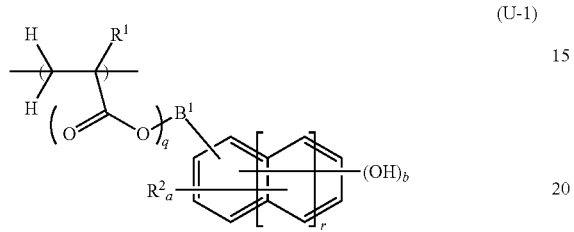

(U-1)

Herein q is 0 or 1, r is an integer of 0 to 2, $R^1$ is hydrogen, fluorine, methyl or trifluoromethyl, $R^2$ is each independently hydrogen or a $C_1$-$C_6$ alkyl group, $B^1$ is a single bond or a $C_1$-$C_{10}$ alkylene group which may contain an ether bond, a is an integer satisfying a≤5+2r−b, and b is an integer of 1 to 3.

Of the recurring units of formula (U-1), those recurring units free of the linker: —CO—O—$B^1$— are derived from monomers of hydroxyl-substituted aromatic ring having a 1-substituted or unsubstituted vinyl group bonded thereto, typically hydroxystyrene units. Preferred examples of such units are those derived from 3-hydroxystyrene, 4-hydroxystyrene, 5-hydroxy-2-vinylnaphthalene and 6-hydroxy-2-vinylnaphthalene.

Those recurring units having the linker: —CO—O—$B^1$— are derived from carbonyl-substituted vinyl monomers, typically (meth)acrylic acid esters. Examples of the recurring units having the linker: —CO—O—$B^1$—, represented by formula (U-1), are shown below.

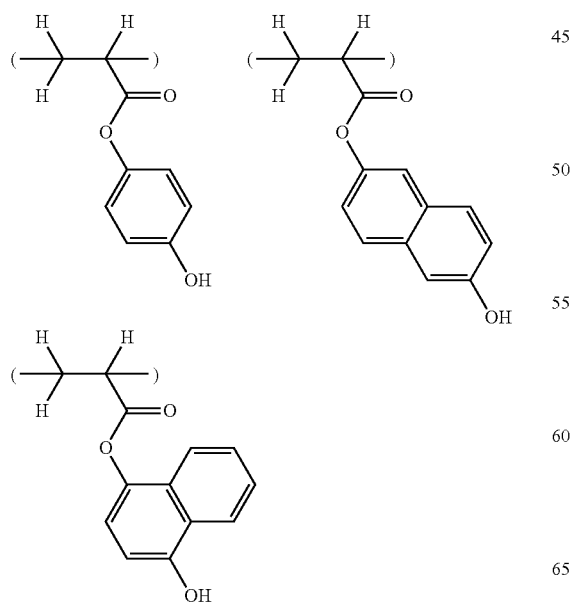

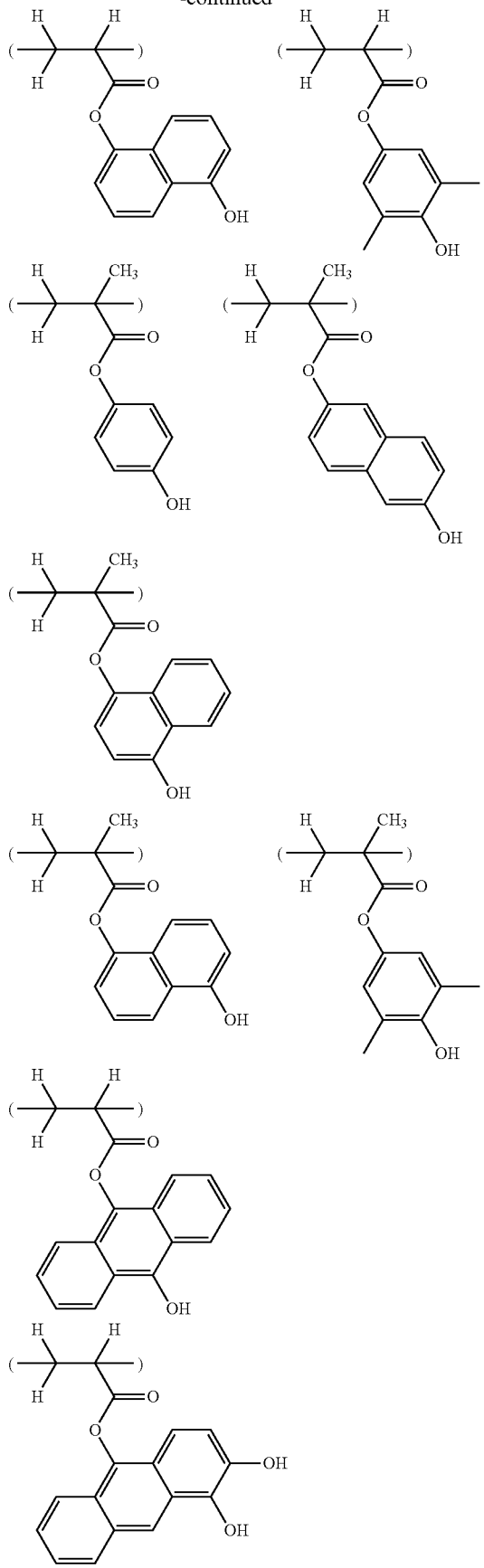

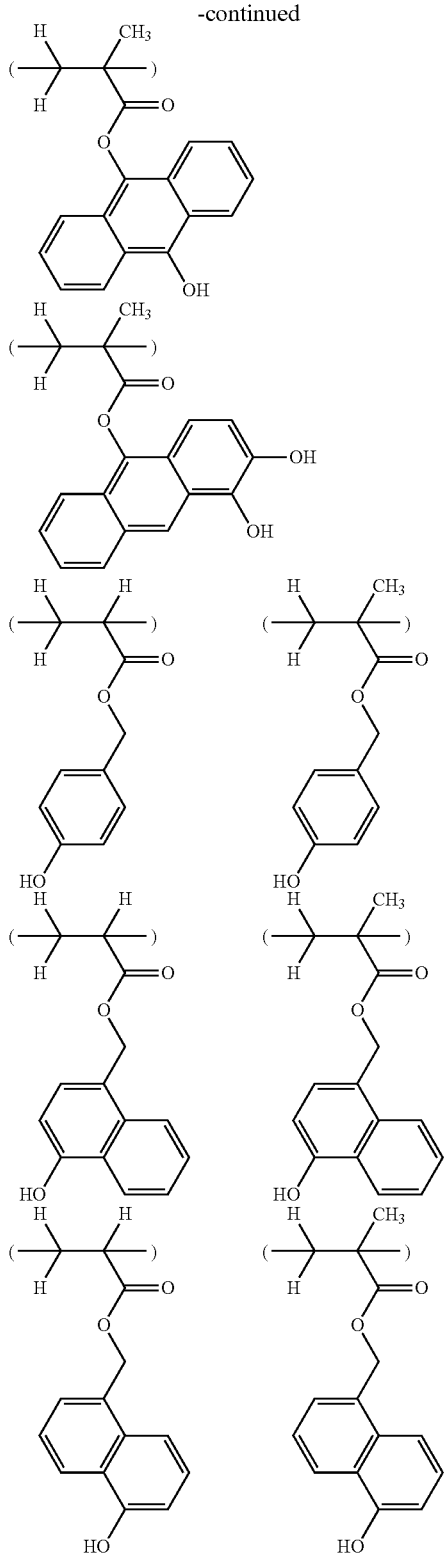

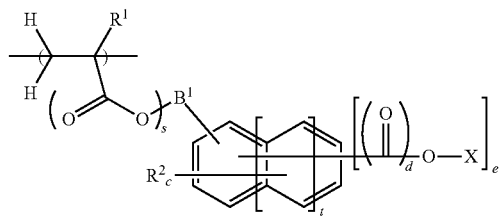

The recurring units having formula (U-1) may be of single type or a combination of plural types and are preferably incorporated in a range of 30 to 90 mol %, more preferably 30 to 80 mol % based on the overall recurring units of the polymer. When units capable of affording higher etch resistance to the polymer, represented by the general formula (U-3) and/or (U-4), as described below, are incorporated in the polymer and they are substituted with a phenolic hydroxyl group, the sum of recurring units having formula (U-1) plus recurring units having formula (U-3) and/or (U-4) should fall in the above-defined range.

In order that the resist composition be of positive tone in that exposed regions of resist film become soluble in aqueous alkaline solution, the polymer should preferably further comprise units having an acid labile group-protected acidic functional group, that is, units which are protected with an acid labile group, but turn alkali soluble under the action of acid. The units which are protected with an acid labile group, but turn alkali soluble under the action of acid are most preferably recurring units having the general formula (U-2).

Herein s is 0 or 1, t is an integer of 0 to 2, $R^1$, $R^2$ and $B^1$ are as defined above, c is an integer satisfying $c \leq 5+2t-e$, d is 0 or 1, e is an integer of 1 to 3, X is an acid labile group when e=1, X is hydrogen or an acid labile group when e=2 or 3, with at least one Y being an acid labile group.

The unit of formula (U-2) corresponds to a unit of formula (U-1) and differs therefrom in that at least one phenolic hydroxyl group substituted on aromatic ring is protected with an acid labile group, or at least one phenolic hydroxyl group is substituted by a carboxyl group which is protected with an acid labile group. The acid labile group may be any of acid labile groups which are eliminatable with acid to give an acidic group, as used in numerous well-known chemically amplified resist compositions. Inter alia, acetal groups are preferred.

Where the phenolic hydroxyl group or carboxyl group mentioned above is protected with a tertiary alkyl group, those alkyl groups of 4 to 18 carbon atoms are preferred because the monomers for polymerization are available via distillation. The alkyl substituents on tertiary carbon of the tertiary alkyl group are typically straight, branched or cyclic alkyl groups of 1 to 15 carbon atoms which may partially contain an oxygen-containing functionality such as ether bond or carbonyl. The alkyl substituents on tertiary carbon may bond together to form a ring.

Preferred examples of the alkyl substituent include, but are not limited to, methyl, ethyl, propyl, adamantyl, norbornyl, tetrahydrofuran-2-yl, 7-oxanorbornan-2-yl, cyclopentyl, 2-tetrahydrofuryl, tricyclo[5.2.1.0$^{2,6}$]decyl, 8-ethyl-8-tricyclo[5.2.1.0$^{2,6}$]decyl, 3-methyl-3-tetracyclo[4.4.0.1$^{2,5}$.1$^{7,10}$]dodecyl, tetracyclo[4.4.0.1$^{2,5}$.1$^{7,10}$]dodecyl, and 3-oxo-1-cyclohexyl. Examples of the tertiary alkyl group include, but are not limited to, tert-butyl, tert-pentyl, 1-ethyl-1-methylpropyl, 1,1-diethylpropyl, 1,1,2-trimethylpropyl, 1-adamantyl-1-methylethyl, 1-methyl-1-(2-norbornyl)ethyl, 1-methyl-1-(tetrahydrofuran-2-yl)ethyl, 1-methyl-1-(7-oxanorbornan-2-yl)ethyl, 1-methylcyclopentyl, 1-ethylcyclopentyl, 1-propylcyclopentyl, 1-cyclopentylcyclopentyl, 1-cyclohexylcyclopentyl, 1-(2-tetrahydrofuryl)cyclopentyl, 1-(7-oxanorbornan-2-yl)cyclopentyl, 1-methylcyclohexyl, 1-ethylcyclohexyl, 1-cyclopentylcyclohexyl, 1-cyclohexylcyclohexyl, 2-methyl-2-norbornyl, 2-ethyl-2-norbornyl, 8-methyl-8-tricyclo[5.2.1.0$^{2,6}$]decyl, 8-ethyl-8-tricyclo[5.2.1.0$^{2,6}$]decyl, 3-methyl-3-tetracyclo [4.4.0.1$^{2,5}$.1$^{7,10}$]dodecyl, 3-ethyl-3-tetracyclo[4.4.0.1$^{2,5}$.1$^{7,10}$]dodecyl, 2-methyl-2-adamantyl, 2-ethyl-2-adamantyl, 1-methyl-3-oxo-1-cyclohexyl, 1-methyl-1-(tetrahydrofuran-2-yl)ethyl, 5-hydroxy-2-methyl-2-adamantyl, and 5-hydroxy-2-ethyl-2-adamantyl.

Acetal groups of the general formula (10):

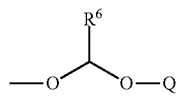
(10)

wherein $R^6$ is hydrogen or a straight, branched or cyclic $C_1$-$C_{10}$ alkyl group, and Q is a straight, branched or cyclic $C_1$-$C_{30}$ alkyl group are often used as the acid labile group. These acetal groups offer a choice of acid labile groups that ensure formation of patterns which are rectangular at the interface between the pattern and the substrate. Acetal groups containing a polycyclic alkyl group of 7 to 30 carbon atoms are preferred for higher resolution. Where Q contains a polycyclic alkyl group, preferably a bond forms between the secondary carbon of the polycyclic structure and the acetal oxygen. This is because the polymer becomes unstable if the bond is on the tertiary carbon of the cyclic structure, suggesting that the resist composition lacks shelf stability and resolution. Inversely, when Q bonds to the acetal oxygen on the primary carbon via straight alkyl of at least one carbon, the polymer may have a low glass transition temperature (Tg), suggesting that the resist pattern after development is degraded in profile by bake.

Examples of the acetal group of formula (10) are shown below.

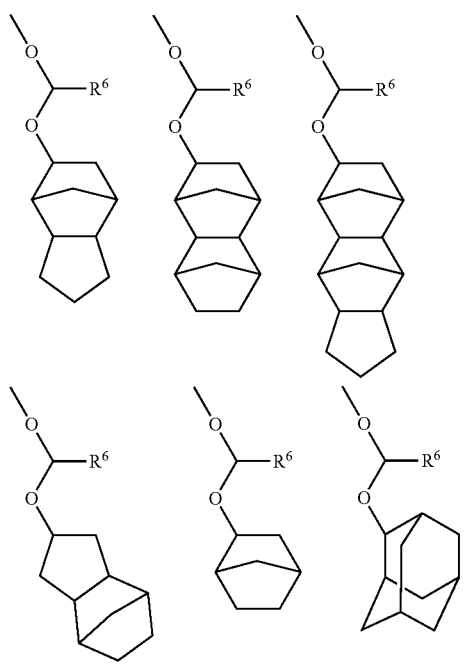

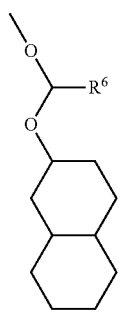

Herein $R^6$ is as defined above.

While $R^6$ is hydrogen or a straight, branched or cyclic $C_1$-$C_{10}$ alkyl group, it is properly selected depending on the design of sensitivity of labile group to acid. For example, if the labile group is designed so as to be decomposed with strong acid while ensuring relatively high stability, then hydrogen is selected. If the labile group is designed to be highly reactive to exhibit high sensitivity to pH changes, a straight alkyl group is selected. If the labile group is substituted at the end with a relatively higher alkyl group and designed to exhibit a large solubility change by decomposition, $R^6$ is preferably an alkyl group whose carbon having a bond to acetal carbon is secondary carbon, although the choice of $R^6$ depends on a combination with the acid generator and basic compound formulated in the resist composition. Examples of group $R^6$ bonding to acetal carbon via secondary carbon include isopropyl, sec-butyl, cyclopentyl, and cyclohexyl.

Another choice of acid labile group is by bonding (—CH$_2$COO-tertiary alkyl group) to a phenolic hydroxyl group. The tertiary alkyl group used herein may be the same as the aforementioned tertiary alkyl group used for the protection of phenolic hydroxyl groups.

The units which are protected with an acid labile group, but turn alkali soluble under the action of acid, represented by formula (U-2), may be used alone or in admixture of two or more. The units of formula (U-2) are preferably incorporated in a range of 5 to 45 mol % based on the overall recurring units of the polymer.

In a preferred embodiment, the polymer may further comprise recurring units having the general formula (U-3) and/or (U-4) as main constituent units.

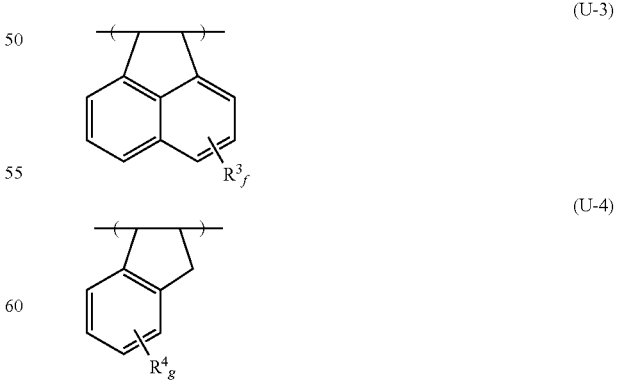

Herein f is an integer of 0 to 6, $R^3$ is each independently hydrogen, or a $C_1$-$C_6$ alkyl group, primary or secondary alkoxy group or $C_1$-$C_7$ alkylcarbonyloxy group which may be substituted with halogen, g is an integer of 0 to 4, and $R^4$ is each independently hydrogen, or a $C_1$-$C_6$ alkyl group, primary or secondary alkoxy group or $C_1$-$C_7$ alkylcarbonyloxy group which may be substituted with halogen.

When the recurring units of at least one type selected from recurring units having formulae (U-3) and (U-4) are incorporated, etching resistance is further improved because not only the aromatic ring possesses etching resistance, but the cyclic structure incorporated into the main chain also exerts the effect of improving resistance to EB irradiation during etching and pattern inspection steps.

The recurring units having formulae (U-3) and (U-4) which incorporate a cyclic structure into the main chain to improve etching resistance may be of one type or a combination of plural types. The units of formulae (U-3) and (U-4) are preferably incorporated in a range of at least 5 mol % based on the overall recurring units of the polymer in order to exert an effect of improving etching resistance. Where the units of formulae (U-3) and (U-4) have a functional group with polarity so that the units are capable of providing adhesion to the substrate, or where the units of formulae (U-3) and (U-4) have a substituent group protected with the aforementioned acid labile group so that the units turn alkali soluble under the action of acid, the amount of these units incorporated is included in the range defined above for the corresponding units. Where the units of formulae (U-3) and (U-4) are free of functional groups or the units of formulae (U-3) and (U-4) have a functional group which is outside the above concept, the amount of these units is preferably up to 30 mol % because the occurrence of development defects is eliminated.

The units of formulae (U-1) and (U-2) and optional units of formulae (U-3) and (U-4) should preferably account for at least 60 mol % of overall monomeric units of the polymer because the range ensures that the polymer provides the resist composition with desired properties. Their amount is more preferably at least 70 mol %, and most preferably at least 85 mol %.

Where all constituent units are units selected from formulae (U-1) to (U-4), the polymer has both high etching resistance and high resolution. Recurring units other than formulae (U-1) to (U-4), which can be incorporated in the polymer, include (meth)acrylate units protected with a customary acid labile group and (meth)acrylate units having an adhesive group, typically lactone structure. Although the properties of a resist film may be finely adjusted by incorporating such other recurring units, the other recurring units are not essential.

Negative Resist Composition

In preparing a chemically amplified negative tone resist composition, a polymer which turns alkali insoluble under the action of acid is used as the base resin. The resin which turns alkali insoluble under the action of acid may be a polymer comprising units which form a crosslinking structure having a higher molecular weight under the action of acid or a polymer which reacts with a crosslinker under the action of acid to form a product having a higher molecular weight.

The base resin is preferably a polymer comprising recurring units having the general formula (U-1), more preferably further comprising recurring units having the general formula (UN-2).

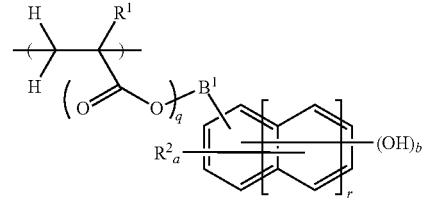

(U-1)

Herein q is 0 or 1, r is an integer of 0 to 2, $R^1$ is hydrogen, fluorine, methyl or trifluoromethyl, $R^2$ is each independently hydrogen or $C_1$-$C_6$ alkyl, $B^1$ is a single bond or $C_1$-$C_{10}$ alkylene which may contain an ether bond, a is an integer satisfying $a \leq 5+2r-b$, and b is an integer of 1 to 3.

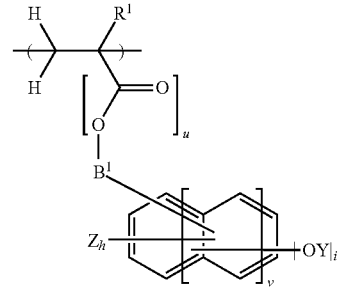

(UN-2)

Herein $R^1$ and $B^1$ are as defined above, Z is hydrogen, or a $C_1$-$C_{20}$ straight, branched or cyclic alkyl, $C_2$-$C_{20}$ hydroxyalkyl, $C_2$-$C_{20}$ alkoxyalkyl, $C_2$-$C_{20}$ alkylthioalkyl, halogen, nitro, cyano, sulfinyl, or sulfonyl group, Y is a $C_1$-$C_{20}$ alkyl or $C_1$-$C_{20}$ acyl group, h is an integer of 0 to 4, i is an integer of 0 to 5, u is 0 or 1, and v is an integer of 0 to 2.

The recurring units of formula (UN-2) impart etch resistance and control the dissolution in an alkaline developer. These recurring units are already found in many resist compositions for the KrF excimer laser lithography and EB lithography.

In formula (UN-2), $B^1$ is a single bond or a $C_1$-$C_{10}$ alkylene group which may be separated by an ether bond (or ethereal oxygen atom). Preferred examples of the alkylene group include methylene, ethylene, propylene, butylene, pentylene, hexylene, and structural isomers of a carbon skeleton having branched or cyclic structure. For the alkylene group containing an ether bond, where u in formula (UN-2) is 1, the ethereal oxygen atom may be incorporated at any position excluding the position between the α- and β-carbons relative to the ester oxygen. Where u is 0, the atom in $B^1$ that bonds with the main chain becomes an ethereal oxygen atom, and a second ethereal oxygen atom may be incorporated at any position excluding the position between the α- and β-carbons relative to that ethereal oxygen atom. Alkylene groups having not more than 10 carbon atoms are desirable because of a sufficient solubility in alkaline developer.

In formula (UN-2), Z is hydrogen, or a $C_1$-$C_{20}$ straight, branched or cyclic alkyl, $C_2$-$C_{20}$ hydroxyalkyl, $C_2$-$C_{20}$ (preferably $C_2$-$C_{10}$) alkoxyalkyl, $C_2$-$C_{20}$ (preferably $C_2$-$C_{10}$) alkylthioalkyl, halogen, nitro, cyano, sulfinyl, or sulfonyl group. Preferred substituent groups Z include hydrogen, halogen atoms such as chlorine, bromine, and iodine, and alkyl groups such as methyl, ethyl, propyl, butyl, pentyl, hexyl and structural isomers thereof, cyclopentyl and cyclohexyl. As long as the carbon count is equal to or less than 20, an appropriate effect of controlling or adjusting (typically reducing) the dissolution of the base resin in alkaline developer is obtainable and the generation of scum or development defects may be suppressed. Of the foregoing preferred substituent groups, such substituent groups as hydrogen, chlorine, bromine, iodine, methyl and ethyl are useful because corresponding monomers may be readily prepared.

In formula (UN-2), Y is a $C_1$-$C_{20}$, preferably $C_1$-$C_6$ alkyl or $C_1$-$C_{20}$, preferably $C_2$-$C_7$ acyl group. When Y is an alkyl group, OY is alkoxy. When Y is an acyl group, OY is acyloxy. Preferred alkoxy groups include methoxy, ethoxy, propoxy, butoxy, pentyloxy, hexyloxy and structural isomers of its hydrocarbon moiety, cyclopentyloxy, and cyclohexyloxy, with methoxy and ethoxy being advantageously used. The acyloxy group may be readily introduced into a polymer even after polymerization, by a chemical modification method and is advantageously utilized for fine adjustment of the dissolution of the base resin in alkaline developer. Preferred acyloxy groups include methylcarbonyloxy, ethylcarbonyloxy, propylcarbonyloxy, butylcarbonyloxy, pentylcarbonyloxy, hexylcarbonyloxy and structural isomers thereof, cyclopentylcarbonyloxy, cyclohexylcarbonyloxy, and benzoyloxy.

In formula (UN-2), h is an integer of 0 to 4, and i is an integer of 0 to 5. Preferably, h is an integer of 0 to 3 and i is an integer of 0 to 3 when v is 0. Also preferably, h is an integer of 0 to 4 and i is an integer of 0 to 5 when v is 1 or 2. The subscript v is an integer of 0 to 2. The structure represents a benzene skeleton when v=0, a naphthalene skeleton when v=1, and an anthracene skeleton when v=2.

Of the recurring units of formula (UN-2), those recurring units wherein u is 0 and $B^1$ is a single bond (meaning that the aromatic ring is directly bonded to the main chain of the polymer), that is, linker-free recurring units are units derived from monomers in which a 1-substituted or unsubstituted vinyl group is attached to an aromatic ring, as typified by styrene skeleton and which are substituted with Z and/or OY. Preferred examples of the basic skeleton include styrene, 4-chlorostyrene, 4-methylstyrene, 4-methoxystyrene, 4-bromostyrene, 4-(2-hydroxypropyl)styrene, 4-(2-hydroxybutyl)styrene, 4-(1-hydroxycyclopentyl)styrene, 4-(2-hydroxy-2-adamantyl)styrene, 2-vinylnaphthalene, and 3-vinylnaphthalene.

Those recurring units wherein u is 1, that is, recurring units having an ester structure as the linker are units of carbonyl-substituted vinyl monomers as typified by (meth)acrylates.

Preferred examples of the units of formula (UN-2) having a linker (—CO—O—$B^1$—) derived from (meth)acrylates are shown below.

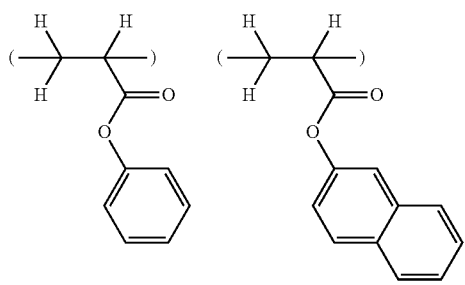

-continued

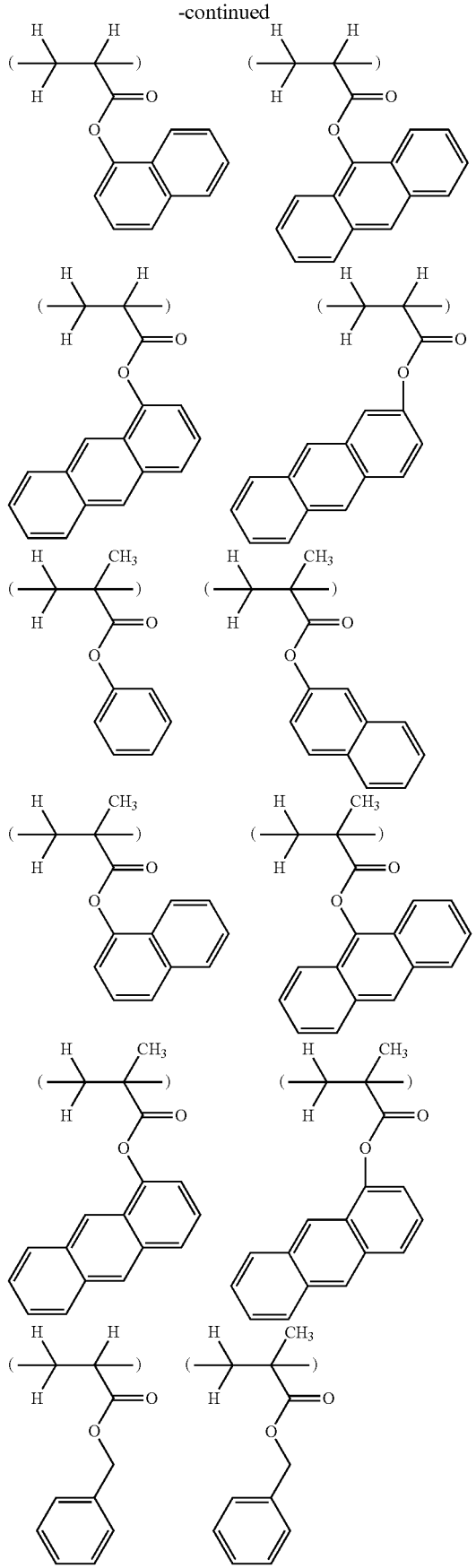

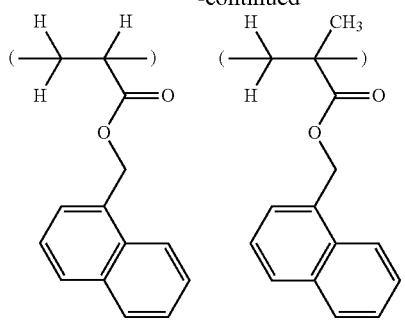
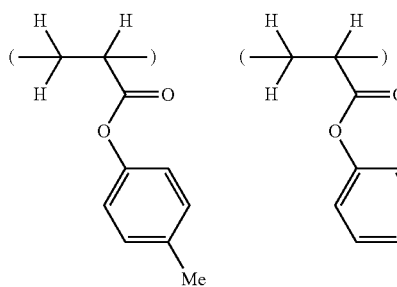
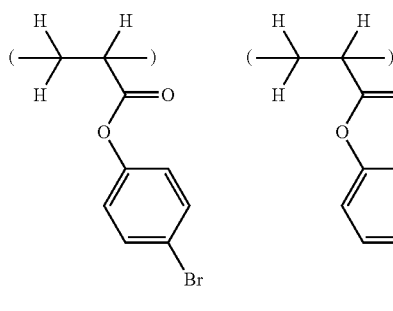
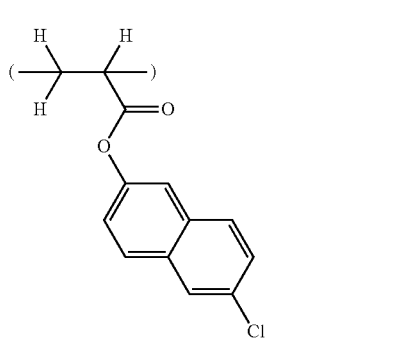
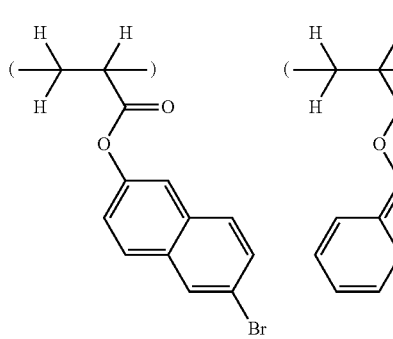

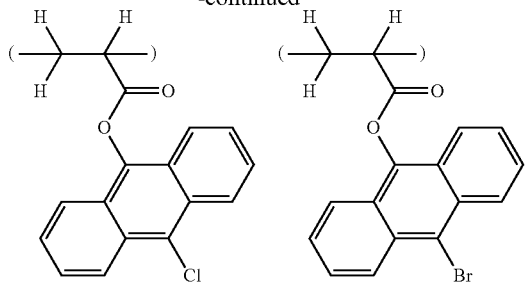
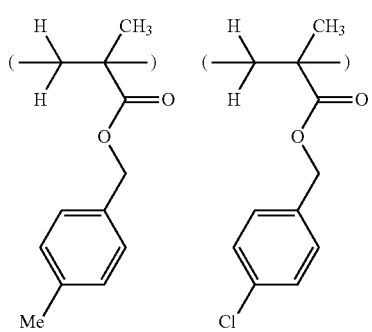
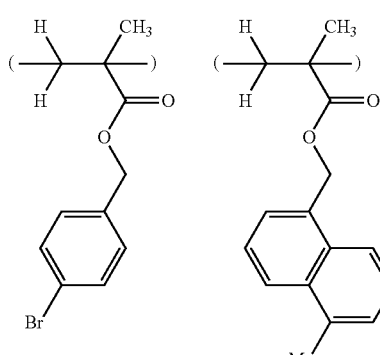
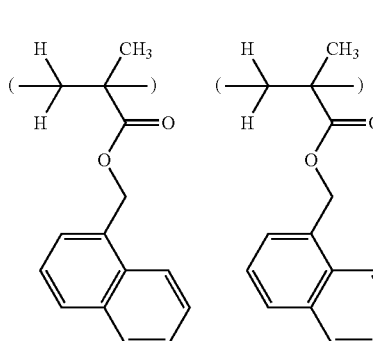

Herein Me stands for methyl.

Preferably the polymer used in the negative resist composition comprises 30 to 90 mol % of recurring units having formula (U-1) and 1 to 45 mol % of recurring units having formula (UN-2) based on the overall recurring units of the polymer.

The polymer used in the negative resist composition may further comprise recurring units having formula (U-3) and/or (U-4) as main constituent units.

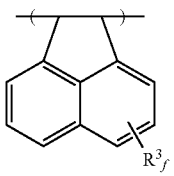

(U-3)

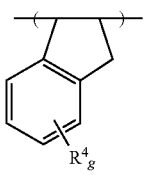

(U-4)

Herein f is an integer of 0 to 6, $R^3$ is each independently hydrogen, or a $C_1$-$C_6$ alkyl group, primary or secondary alkoxy group or $C_1$-$C_7$ alkylcarbonyloxy group which may be substituted with halogen, g is an integer of 0 to 4, and $R^4$ is each independently hydrogen, or a $C_1$-$C_6$ alkyl group, primary or secondary alkoxy group or $C_1$-$C_7$ alkylcarbonyloxy group which may be substituted with halogen.

When the recurring units of at least one type selected from recurring units having formulae (U-3) and (U-4) are incorporated, etching resistance is further improved because not only the aromatic ring possesses etching resistance, but the cyclic structure incorporated into the main chain also exerts the effect of improving resistance to EB irradiation during etching and pattern inspection steps.

The recurring units having formulae (U-3) and (U-4) which incorporate a cyclic structure into the main chain to improve etching resistance may be of one type or a combination of plural types. The units of formulae (U-3) and (U-4) are preferably incorporated in a range of at least 5 mol % based on the overall recurring units of the polymer in order to exert an effect of improving etching resistance. Where the units of formulae (U-3) and (U-4) have a functional group with polarity so that the units are capable of providing adhesion to the substrate, or where the units of formulae (U-3) and (U-4) have a substituent group protected with the aforementioned acid labile group so that the units turn alkali soluble under the action of acid, the amount of these units incorporated is included in the range defined above for the corresponding units. Where the units of formulae (U-3) and (U-4) are free of functional groups or the units of formulae (U-3) and (U-4) have a functional group which is outside the above concept, the amount of these units is preferably up to 30 mol % because the occurrence of development defects is eliminated.

In the chemically amplified negative resist composition, a crosslinker may be blended for forming or strengthening the crosslinking structure of the base resin. Suitable crosslinkers which can be used herein include melamine compounds, guanamine compounds, glycoluril compounds and urea compounds having substituted thereon at least one group selected from among methylol, alkoxymethyl and acyloxymethyl groups, epoxy compounds, isocyanate compounds, azide compounds, and compounds having a double bond such as an alkenyl ether group. While these compounds may be used as an additive, they may be incorporated into the polymer side chain as pendant. Hydroxyl-containing compounds may also be used as the crosslinker.

Of the foregoing compounds, examples of suitable epoxy compounds include tris(2,3-epoxypropyl)isocyanurate, trimethylolmethane triglycidyl ether, trimethylolpropane triglycidyl ether, and triethylolethane triglycidyl ether. Examples of the melamine compound include hexamethylol melamine, hexamethoxymethyl melamine, hexamethylol melamine compounds having 1 to 6 methylol groups methoxymethylated and mixtures thereof, hexamethoxyethyl melamine, hexaacyloxymethyl melamine, hexamethylol melamine compounds having 1 to 6 methylol groups acyloxymethylated and mixtures thereof. Examples of the guanamine compound include tetramethylol guanamine, tetramethoxymethyl guanamine, tetramethylol guanamine compounds having 1 to 4 methylol groups methoxymethylated and mixtures thereof, tetramethoxyethyl guanamine, tetraacyloxyguanamine, tetramethylol guanamine compounds having 1 to 4 methylol groups acyloxymethylated and mixtures thereof. Examples of the glycoluril compound include tetramethylol glycoluril, tetramethoxyglycoluril, tetramethoxymethyl glycoluril, tetramethylol glycoluril compounds having 1 to 4 methylol groups methoxymethylated and mixtures thereof, tetramethylol glycoluril compounds having 1 to 4 methylol groups acyloxymethylated and mixtures thereof. Examples of the urea compound include tetramethylol urea, tetramethoxymethyl urea, tetramethylol urea compounds having 1 to 4 methylol groups methoxymethylated and mixtures thereof, and tetramethoxyethyl urea.

Examples of the isocyanate compound include tolylene diisocyanate, diphenylmethane diisocyanate, hexamethylene diisocyanate, and cyclohexane diisocyanate. Examples of the azide compound include 1,1'-biphenyl-4,4'-bisazide, 4,4'-methylidenebisazide, and 4,4'-oxybisazide.

Examples of the alkenyl ether group-containing compound include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylol propane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylol propane trivinyl ether.

The crosslinker may be preferably blended in an amount of 0 to 50 parts, more preferably 5 to 50 parts, and even more preferably 10 to 30 parts by weight per 100 parts by weight of the base resin. The crosslinker may be used alone or in admixture. When used, at least 5 parts of the crosslinker is effective for improving resolution and up to 50 parts of the crosslinker eliminates the risks of bridging between pattern features and losing resolution.

Independent of whether the resist composition is positive or negative, a basic compound may be contained in the resist composition. It is typically an amine compound having a carboxyl group, but free of hydrogen in covalent bond with nitrogen serving as basic center.

In pattern formation, the problem that the pattern profile changes in proximity to the substrate depending on the material of the processable substrate is known as pattern's substrate dependency. As the size of the desired pattern is reduced, even a small change of shape is a problem. Particularly in the processing of a photomask blank, when a chemically amplified negative resist composition is used to form a pattern on the outermost surface layer of chromium oxynitride in the photomask blank, a notch is introduced in the pattern where it is in contact with the substrate, that is, undercut occurs. However, the inclusion of an amine compound having a carboxyl group, but free of hydrogen in covalent bond with nitrogen serving as basic center is effective for preventing the undercut.

By contrast, an amine compound having a carboxyl group and hydrogen in covalent bond with nitrogen serving as basic center, like a primary amine, does not exert the effect of mitigating undercuts on the substrate. To maximize the effect, a tertiary amine free of hydrogen in covalent bond with nitrogen serving as basic center is preferred.

Of the tertiary amine compounds, those compounds exhibiting higher basicity than the amine compounds in which the basic center is nitrogen contained in an aromatic ring, and which are weak bases, such as 2-quinolinecarboxylic acid and nicotinic acid are more advantageous in that since carboxyl groups well orient on the substrate side, they prevent the acid generated by the PAG from diffusing to the substrate and eventually being deactivated.

The undercut problem often arises on substrates whose surface material is a nitride compound such as TiN, SiN or SiON. This is true particularly when the substrate surface is of a metal chromium-based compound, which may be either metal chromium or a chromium compound containing nitrogen and/or oxygen, and at worse, it is difficult to overcome the undercut problem in this situation. By contrast, the resist composition having the basic compound blended therein enables to form a pattern of satisfactory profile even on a substrate whose outermost surface is of a chromium-based compound. Thus it is advantageously used in processing of photomask blanks and the like.

With respect to the chemical structure of the amine compound having a carboxyl group, but free of hydrogen in covalent bond with nitrogen serving as basic center, preferred examples include amine compounds and amine oxide compounds of the general formulae (7) to (9), but are not limited thereto.

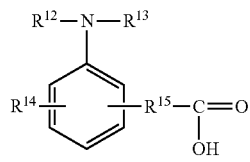
(7)

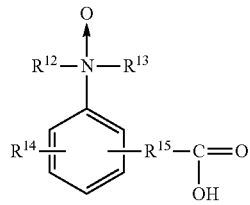
(8)

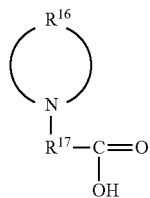
(9)

Herein $R^{12}$ and $R^{13}$ are each independently a straight, branched or cyclic $C_1$-$C_{20}$ alkyl group, $C_6$-$C_{20}$ aryl group, $C_7$-$C_{20}$ aralkyl group, $C_2$-$C_{20}$ hydroxyalkyl group, $C_2$-$C_{20}$ alkoxyalkyl group, $C_2$-$C_{20}$ acyloxyalkyl group, or $C_2$-$C_{20}$ alkylthioalkyl group, or $R^{12}$ and $R^{13}$ may bond together to form a cyclic structure with the nitrogen atom to which they are attached. $R^{14}$ is hydrogen, a straight, branched or cyclic $C_1$-$C_{20}$ alkyl group, $C_6$-$C_{20}$ aryl group, $C_7$-$C_{20}$ aralkyl group, $C_2$-$C_{20}$ hydroxyalkyl group, $C_2$-$C_{20}$ alkoxyalkyl group, $C_2$-$C_{20}$ acyloxyalkyl group, $C_2$-$C_{20}$ alkylthioalkyl group, or halogen. $R^{15}$ is a single bond, a straight, branched or cyclic $C_1$-$C_{20}$ alkylene group, or $C_6$-$C_{20}$ arylene group. $R^{16}$ is an optionally substituted, straight or branched $C_2$-$C_{20}$ alkylene group whose carbon-carbon linkage may be separated by at least one carbonyl (—CO—), ether (—O—), ester (—COO—) or sulfide (—S—) group. $R^{17}$ is a straight, branched or cyclic $C_1$-$C_{20}$ alkylene group or $C_6$-$C_{20}$ arylene group.

Exemplary groups in formulae (7) to (9) are given below, but not limited thereto. Suitable straight, branched or cyclic $C_1$-$C_{20}$ alkyl groups include methyl, ethyl, propyl, isopropyl, butyl, isobutyl, t-butyl, pentyl, hexyl, decyl, cyclopentyl, cyclohexyl, and decahydronaphthalenyl. Suitable $C_6$-$C_{20}$ aryl groups include phenyl, naphthyl, anthryl, phenanthryl, pyrenyl, naphthacenyl, and fluorenyl. Suitable $C_7$-$C_{20}$ aralkyl groups include benzyl, phenethyl, phenylpropyl, naphthylmethyl, naphthylethyl, and anthracenylmethyl. Suitable $C_2$-$C_{20}$, preferably $C_2$-$C_{10}$ hydroxyalkyl groups include hydroxymethyl, hydroxyethyl, and hydroxypropyl. Suitable $C_2$-$C_{20}$, preferably $C_2$-$C_{10}$ alkoxyalkyl groups include methoxymethyl, ethoxymethyl, propoxymethyl, isopropoxymethyl, butoxymethyl, isobutoxymethyl, t-butoxymethyl, t-amyloxymethyl, cyclohexyloxymethyl, and cyclopentyloxymethyl. Suitable $C_2$-$C_{20}$, preferably $C_2$-$C_{10}$ acyloxyalkyl groups include formyloxymethyl, acetoxymethyl, propionyloxymethyl, butyryloxymethyl, pivaloyloxymethyl, cyclohexanecarbonyloxymethyl, and decanoyloxymethyl. Suitable $C_2$-$C_{20}$, preferably $C_2$-$C_{10}$ alkylthioalkyl groups include methyithiomethyl, ethylthiomethyl, propylthiomethyl, isopropylthiomethyl, butylthiomethyl, isobutylthiomethyl, t-butylthiomethyl, t-amylthiomethyl, decyithiomethyl, and cyclohexylthiomethyl.

Preferred examples of the amine compound of formula (7) include, but are not limited thereto, o-dimethylaminobenzoic acid, p-dimethylaminobenzoic acid, m-dimethylaminobenzoic acid, p-diethylaminobenzoic acid, p-dipropylaminobenzoic acid, p-diisopropylaminobenzoic acid, p-dibutylaminobenzoic acid, p-dipentylaminobenzoic acid, p-dihexylaminobenzoic acid, p-diethanolaminobenzoic acid, p-diisopropanolaminobenzoic acid, p-dimethanolaminobenzoic acid, 2-methyl-4-diethylaminobenzoic acid, 2-methoxy-4-diethylaminobenzoic acid, 3-dimethylamino-2-naphthalenic acid, 3-diethylamino-2-naphthalenic acid, 2-dimethylamino-5-bromobenzoic acid, 2-dimethylamino-5-chlorobenzoic acid, 2-dimethylamino-5-iodobenzoic acid, 2-dimethylamino-5-hydroxybenzoic acid, 4-dimethylaminophenylacetic acid, 4-dimethylaminophenylpropionic acid, 4-dimethylaminophenylbutyric acid, 4-dimethylaminophenylmalic acid, 4-dimethylaminophenylpyruvic acid, 4-dimethylaminophenyllactic acid, 2-(4-dimethylaminophenyl)benzoic acid, and 2-(4-(dibutylamino)-2-hydroxybenzoyl)benzoic acid.

Preferred examples of the amine oxide compound of formula (8) include oxidized forms of exemplary compounds of formula (7), but are not limited thereto.

Preferred examples of the amine compound of formula (9) include, but are not limited thereto, 1-piperidinepropionic acid, 1-piperidinebutyric acid, 1-piperidinemalic acid, 1-piperidinepyruvic acid, and 1-piperidinelactic acid.

The chemically amplified negative resist composition may contain one or more basic compounds selected from the aforementioned amine and amine oxide compounds.

The polymers used as the base resin in the chemically amplified positive and negative resist compositions may be prepared by any well-known methods, for example, by selecting suitable monomers, and copolymerizing them while protection and deprotection reactions may be combined if necessary. The copolymerization reaction is preferably radical or anion polymerization, but not limited thereto. For the polymerization reaction, reference should be made to, for example, WO 2006/121096, JP-A 2008-102383, JP-A 2008-304590, and JP-A 2004-115630.

The polymer should preferably have a weight average molecular weight (Mw) in the range of 2,000 to 50,000, and more preferably 3,000 to 20,000, as measured by gel permeation chromatography (GPC) versus polystyrene standards using tetrahydrofuran solvent. As long as Mw is at least 2,000, a phenomenon that pattern top is rounded to invite a drop of resolution and degradation of LER as is known in the art is eliminated. If Mw increases beyond the necessity, there is a tendency to increase LER, though depending on a particular pattern to be resolved. It is thus recommended to control the Mw to 50,000 or lower, with a Mw of 20,000 or lower being preferred particularly when it is desired to form a pattern with a line width of up to 100 nm.

The polymer should preferably have a narrow dispersity (Mw/Mn) of 1.0 to 2.0, especially 1.0 to 1.8. The narrow dispersity eliminates a possibility that foreign matter is left on the pattern or the pattern profile is degraded after development.

The polymer is advantageously used as a base resin in the resist composition along with the inventive sulfonium salt. The resist composition may exert fundamental resist performance when a solvent is added thereto. If necessary, a basic compound, acid generator (other than the inventive sulfonium salt), another polymer, surfactant, and the like may be added.

When the inventive polymer comprising units selected from formulae (U-1) to (U-4) and formula (UN-2) and the other polymer are used in blend, the inventive polymer should preferably account for at least 30%, more preferably at least 50% by weight of the polymer blend. Use of at least 30% by weight of the inventive polymer is preferred because the formation of defects during development is prevented. However, it is also preferred to blend the inventive polymer in such an amount that the proportion of aromatic ring-bearing units may not fall below 60 mol % based on overall recurring units of polymers in the blend. The other polymer is not limited to one type and a mixture of two or more polymers may be added. The use of plural polymers allows for adjustment of resist properties.

Optionally, the resist composition of the invention may further comprise a surfactant which is commonly used for facilitating the coating operation. It may be selected from numerous well-known surfactants as described in WO 2006/121096, JP-A 2008-102383, JP-A 2008-304590, JP-A 2004-115630, and JP-A 2005-008766 and in accordance with the teaching thereof. The surfactant may be added in an amount of preferably up to 2 parts, more preferably 0.01 to 1 part by weight per 100 parts by weight of the base resin.

Patterning Process

For pattern formation from the resist composition, any well-known lithography processes may be used. In general, the resist composition is applied onto a substrate on which an integrated circuit is to be formed (e.g., Si, $SiO_2$, SiN, SiON, TiN, WSi, BPSG, SOG or organic antireflective coating) or a substrate on which a mask circuit is to be formed (e.g., Cr, CrO, CrON or MoSi) by a suitable coating technique, typically spin coating. The coating is prebaked on a hot plate at a temperature of 60 to 150° C. for 1 to 20 minutes, preferably 80 to 140° C. for 1 to 10 minutes. The resulting resist film is typically 0.05 to 2.0 μm thick.

With a mask having a desired pattern placed above the resist film, the resist film is then exposed to high-energy radiation such as deep-UV, excimer laser light, x-ray or EB in an exposure dose preferably in the range of 1 to 200 $mJ/cm^2$, more preferably 10 to 100 $mJ/cm^2$. Alternatively, a pattern may be directly written with a beam, typically EB, without a need for mask. The chemically amplified resist composition of the invention is advantageous particularly on patternwise exposure to EUV or EB. Light exposure may be done by a conventional lithography process or in some cases, by an immersion lithography process of providing liquid immersion, typically water, between the mask and the resist film. In the case of immersion lithography, a protective film which is insoluble in water may be used.

The resist film is further baked (PEB) on a hot plate at 60 to 150° C. for 1 to 20 minutes, preferably 80 to 140° C. for 1 to 5 minutes. Thereafter the resist film is developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle or spray techniques. In this way, a desired resist pattern is formed on the substrate.

The resist composition of the invention is advantageous particularly on use under the situation that requires high etching resistance, and a minimal change of pattern line width and minimal LER even when the time duration from exposure to PEB is prolonged. It is also advantageous for pattern formation on a processable substrate, typically a substrate having a surface layer of material to which the resist pattern is less adherent with a likelihood of pattern stripping or pattern collapse, specifically a substrate having sputter deposited thereon a layer of metallic chromium or a chromium compound containing one or more light elements such as oxygen, nitrogen and carbon, more specifically a photomask blank.

EXAMPLE

Examples and Comparative Examples are given below by way of illustration and not by way of limitation. All parts are by weight (pbw); Me stands for methyl; Mw is a weight average molecular weight as measured by GPC versus polystyrene standards. The copolymer compositional ratio is a molar ratio.

Synthesis Example 1

Synthesis of Sulfonium Salt

Sulfonium salts PAG-1 to PAG-9 within the scope of the invention were synthesized according to the scheme shown below. The structure of the inventive sulfonium salts PAG-1 to PAG-9 is shown in Table 5, and the structure of comparative sulfonium salts c-PAG-1 to c-PAG-3 shown in Table 6.

Synthesis Example 1-1

Synthesis of triphenylsulfonium 4-(2,4,6-triisopropyl-benzenesulfonyloxy)benzenesulfonate (PAG-1)

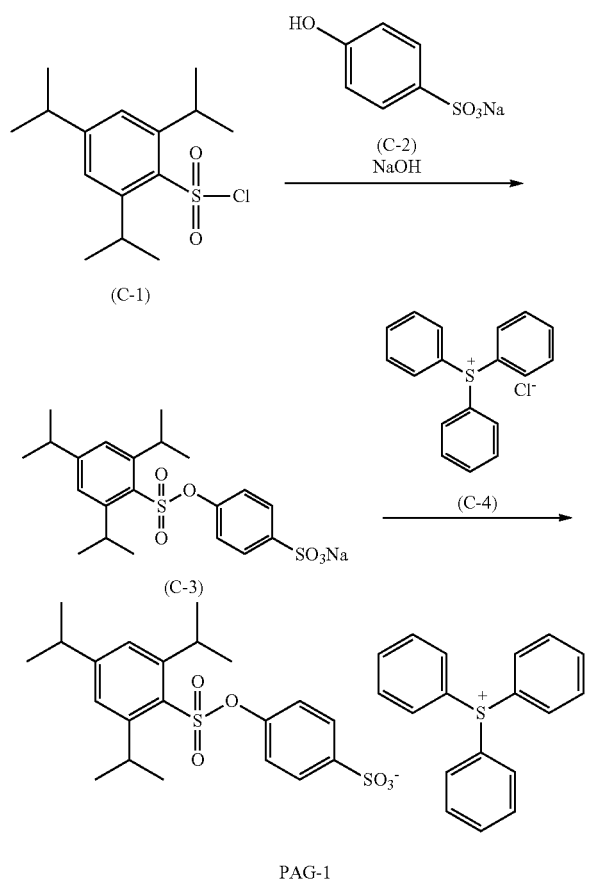

In 20 g of tetrahydrofuran and 15 g of H$_2$O was suspended 4.32 g of sodium 4-hydroxybenzenesulfonate (C-2). Under ice cooling, 3.20 g of 25 wt % NaOH was added dropwise to the suspension, which was stirred for 1 hour. A tetrahydrofuran solution of 3.03 g of 2,4,6-triisopropylbenzenesulfonyl chloride (C-1) was added dropwise to the solution, which was stirred for 3 hours at room temperature until compound (C-3) was obtained. Next, an aqueous solution of 50 g of triphenylsulfonium chloride (C-4) and 50 g of methylene chloride were added to the reaction solution. After 30 minutes of stirring, the organic layer was taken out, washed with water, and concentrated in reduced pressure. Methyl isobutyl ketone was added to the concentrate, which was concentrated again. The precipitated solid was washed with diisopropyl ether and dried in vacuum. The target compound was obtained, i.e., 3.02 g of triphenylsulfonium 4-(2,4,6-triisopropylbenzenesulfonyloxy)benzenesulfonate, designated PAG-1, as white crystal (yield 43%).

Synthesis Example 1-2

Synthesis of triphenylsulfonium 4-(2,4,6-triisopropyl-benzoyloxy)benzenesulfonate (PAG-2)

Synthesis was carried out as in Synthesis Example 1-1 aside from using 2,4,6-triisopropylbenzoyl chloride instead of 2,4,6-triisopropylbenzenesulfonyl chloride (C-1). There was obtained 2.89 g of PAG-2 (yield 51%).

Synthesis Example 1-3

Synthesis of triphenylsulfonium 4-(2,4,6-tricyclohexyl-benzenesulfonyloxy)benzenesulfonate (PAG-3)

Synthesis was carried out as in Synthesis Example 1-1 aside from using 2,4,6-tricyclohexylbenzenesulfonyl chloride instead of 2,4,6-triisopropylbenzenesulfonyl chloride (C-1). There was obtained 3.19 g of PAG-3 (yield 55%).

Synthesis Example 1-4

Synthesis of triphenylsulfonium 2,6-diisopropyl-4-(2,4,6-tricyclohexylbenzenesulfonyloxy)benzenesulfonate (PAG-4)

Synthesis was carried out as in Synthesis Example 1-1 aside from using 2,4,6-tricyclohexylbenzenesulfonyl chloride instead of 2,4,6-triisopropylbenzenesulfonyl chloride (C-1), and sodium 2,6-diisopropyl-4-hydroxybenzenesulfonate instead of sodium 4-hydroxybenzenesulfonate (C-2). There was obtained 3.09 g of PAG-4 (yield 53%).

Synthesis Example 1-5

Synthesis of 10-phenylphenoxathiinium 4-(2,4,6-triisopropylbenzenesulfonyloxy)benzenesulfonate (PAG-5)

Synthesis was carried out as in Synthesis Example 1-1 aside from using 10-phenylphenoxathiinium chloride instead of triphenylsulfonium chloride (C-4). There was obtained 2.75 g of PAG-5 (yield 48%).

Synthesis Example 1-6

Synthesis of 10-phenylphenoxathiinium 2-isopropyl-5-methyl-4-(2,4,6-tricyclohexylbenzoyloxy)benzenesulfonate (PAG-6)

Synthesis was carried out as in Synthesis Example 1-1 aside from using 2,4,6-tricyclohexylbenzoyl chloride instead of 2,4,6-triisopropylbenzenesulfonyl chloride (C-1), sodium 2-isopropyl-5-methyl-4-hydroxybenzenesulfonate instead of sodium 4-hydroxybenzenesulfonate (C-2), and 10-phenylphenoxathiinium chloride instead of triphenylsulfonium chloride (C-4). There was obtained 3.10 g of PAG-6 (yield 49%).

Synthesis Example 1-7

Synthesis of 4-tert-butylphenyldiphenylsulfonium 4-(2,4,6-triisopropylbenzenesulfonyloxy)benzenesulfonate (PAG-7)

Synthesis was carried out as in Synthesis Example 1-1 aside from using 4-tert-butylphenyldiphenylsulfonium chloride instead of triphenylsulfonium chloride (C-4). There was obtained 3.11 g of PAG-7 (yield 45%).

Synthesis Example 1-8

Synthesis of 10-phenylphenoxathiinium 4-(2,4,6-triisopropylbenzenesulfonyloxy)ethanesulfonate (PAG-8)

Synthesis was carried out as in Synthesis Example 1-1 aside from using triethylammonium hydroxyethanesulfonate instead of sodium 4-hydroxybenzenesulfonate (C-2), and 10-phenylphenoxathiinium chloride instead of triphenylsulfonium chloride (C-4). There was obtained 2.75 g of PAG-8 (yield 34%).

Synthesis Example 1-9

Synthesis of 10-phenylphenoxathiinium 4-(2,4,6-tricyclohexylbenzoyloxy)ethanesulfonate (PAG-9)

Synthesis was carried out as in Synthesis Example 1-1 aside from using 2,4,6-tricyclohexylbenzoyl chloride instead of 2,4,6-triisopropylbenzenesulfonyl chloride (C-1), triethylammonium hydroxyethanesulfonate instead of sodium 4-hydroxybenzenesulfonate (C-2), and 10-phenylphenoxathiinium chloride instead of triphenylsulfonium chloride (C-4). There was obtained 3.10 g of PAG-9 (yield 32%).

Synthesis Example 2

Synthesis of Positive Resist Polymers

Polymers for use in positive resist compositions were synthesized according to the following formulation. The compositional proportion (in molar ratio) of polymers is shown in Table 1. The structure of recurring units is shown in Tables 2 to 4.

Synthesis Example 2-1

Synthesis of Polymer 1

A 3-L flask was charged with 407.5 g of acetoxystyrene, 42.5 g of acenaphthylene, and 1,275 g of toluene as solvent. The reactor was cooled at −70° C. in a nitrogen atmosphere, after which vacuum pumping and nitrogen blow were repeated three times. The reactor was warmed up to room temperature, whereupon 34.7 g of 2,2'-azobis(2,4-dimethylvaleronitrile) (V-65 by Wako Pure Chemical Industries, Ltd.) was added. The reactor was heated at 55° C., whereupon reaction ran for 40 hours. With stirring, a mixture of 970 g of methanol and 180 g of water was added dropwise to the reaction solution. After 30 minutes, the lower layer (polymer layer) was concentrated under reduced pressure. The polymer layer concentrate was dissolved again in 0.45 L of methanol and 0.54 L of THF, to which 160 g of triethylamine and 30 g of water were added. The reaction mixture was heated at 60° C. for 40 hours for deprotection reaction. The reaction solution was concentrated under reduced pressure. To the concentrate, 548 g of methanol and 112 g of acetone were added for dissolution. With stirring, 990 g of hexane was added dropwise to the solution. After 30 minutes, 300 g of THF was added to the lower layer (polymer layer). With stirring, 1,030 g of hexane was added dropwise thereto. After 30 minutes, the lower layer (polymer layer) was concentrated under reduced pressure. The polymer solution was neutralized with 82 g of acetic acid. The reaction solution was concentrated, dissolved in 0.3 L of acetone, and poured into 10 L of water for precipitation. The precipitate was filtered and dried, yielding 280 g of a white polymer. The polymer was analyzed by $^1$H-NMR and GPC, with the results shown below.

Copolymer Compositional Ratio
hydroxystyrene:acenaphthylene=89.3:10.7
Mw=5,000
Mw/Mn=1.63

Under acidic conditions, 100 g of the polymer was reacted with 50 g of 2-methyl-1-propenyl methyl ether. This was followed by neutralization, separatory operation, and crystallization, obtaining 125 g of a polymer, designated Polymer 1.

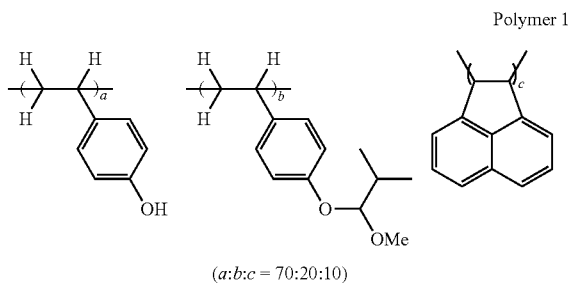

Polymer 1

$(a:b:c = 70:20:10)$

Synthesis Example 2-2

Synthesis of Polymer 2

Polymer 2 was synthesized by the same procedure as in Synthesis Example 2-1 aside from using 2-methyl-1-propenyl 8-tricyclo[5.2.1.0$^{2,6}$]decanyl ether instead of 2-methyl-1-propenyl methyl ether.

Synthesis Example 2-3

Synthesis of Polymer 3

Polymer 3 was synthesized by the same procedure as in Synthesis Example 2-1 aside from using 2-methyl-1-propenyl 2-adamantyl ether instead of 2-methyl-1-propenyl methyl ether.

Synthesis Example 2-4

Synthesis of Polymer 4

In nitrogen atmosphere, 362 g of 4-hydroxyphenyl methacrylate, 38.2 g of acenaphthylene, 40.9 g of dimethyl 2,2'-azobis(2-methylpropionate) (V-601 by Wako Pure Chemical Industries, Ltd.), and 500 g of methyl ethyl ketone were fed into a dropping cylinder to form a monomer solution. A flask in nitrogen atmosphere was charged with 250 g of methyl ethyl ketone, which was heated at 80° C. with stirring. With stirring, the monomer solution was added dropwise to the flask over 4 hours. After the completion of dropwise addition, the polymerization solution was continuously stirred for 4 hours while maintaining its temperature at 80° C. The polymerization solution was cooled to room temperature, whereupon it was added dropwise to 10 kg of hexane/diisopropyl ether solution. The precipitate was collected by filtration, washed twice with 5 kg of hexane, and vacuum dried at 50° C. for 20 hours, obtaining a copolymer in white powder solid form. Under acidic conditions, 100 g of the polymer was reacted with 40.5 g of 2-methyl-1-propenyl methyl ether. This was followed by neutralization, separatory operation, and crystallization, obtaining 128 g of a polymer, designated Polymer 4.

Synthesis Example 2-5

Synthesis of Polymer 5

Polymer 5 was synthesized by the same procedure as in Synthesis Example 2-4 aside from using 2-methyl-1-propenyl 8-tricyclo[5.2.1.0$^{2,6}$]decanyl ether instead of 2-methyl-1-propenyl methyl ether.

Synthesis Example 2-6

Synthesis of Polymer 6

Polymer 6 was synthesized by the same procedure as in Synthesis Example 2-4 aside from using 2-methyl-1-propenyl 2-adamantyl ether instead of 2-methyl-1-propenyl methyl ether.

Synthesis Examples 2-7 to 2-12

Synthesis of Polymers 7 to 12

Polymers containing hydroxystyrene units in Table 1 were synthesized by the same procedure as in Synthesis Example 2-1, 2-2 or 2-3 aside from changing the type and amount of monomers. Polymers containing 4-hydroxyphenyl methacrylate units in Table 1 were synthesized by the same procedure as in Synthesis Example 2-4, 2-5 or 2-6 aside from changing the type and amount of monomers.

Synthesis Example 2-13

Synthesis of Polymer 13

In nitrogen atmosphere, 42.4 g of 4-hydroxyphenyl methacrylate, 40.6 g of 5-oxo-4-oxatricyclo[4.2.1.0$^{3,7}$]nonan-2-yl methacrylate, 16.9 g of 1-methoxy-2-methyl-1-propyl methacrylate, 9.3 g of dimethyl 2,2'-azobis(2-methylpropionate) (V-601 by Wako Pure Chemical Industries, Ltd.), and 124 g of methyl ethyl ketone were fed into a dropping cylinder to form a monomer solution. A flask in nitrogen atmosphere was charged with 62 g of methyl ethyl ketone, which was heated at 80° C. with stirring. With stirring, the monomer solution was added dropwise to the flask over 4 hours. After the completion of dropwise addition, the polymerization solution was continuously stirred for 4 hours while maintaining its temperature at 80° C. The polymerization solution was cooled to room temperature, whereupon it was added dropwise to 1.5 kg of hexane/diisopropyl ether solution. The precipitate was collected by filtration, washed twice with 300 g of hexane, and vacuum dried at 50° C. for 20 hours, obtaining a copolymer in white powder solid form. It is designated Polymer 13.

Synthesis Examples 2-14 and 2-15

Synthesis of Polymers 14 and 15

Polymers in Table 1 were synthesized by the same procedure as in Synthesis Example 2-13 aside from changing the type and amount of monomers.

Synthesis Example 2-16

Synthesis of Polymer 16

In nitrogen atmosphere, 64.8 g of 4-acetoxystyrene, 9.1 g of acenaphthylene, 26.1 g of amyloxystyrene, 11.0 g of dimethyl 2,2'-azobis(2-methylpropionate) (V-601), and 150 g of methyl ethyl ketone were fed into a dropping cylinder to form a monomer solution. A flask in nitrogen atmosphere was charged with 75 g of methyl ethyl ketone, which was heated at 80° C. with stirring. With stirring, the monomer solution was added dropwise to the flask over 4 hours. After the completion of dropwise addition, the polymerization solution was continuously stirred for 18 hours while maintaining its temperature at 80° C. The polymerization solution was cooled to room temperature, whereupon it was added dropwise to 1.5 kg of hexane/diisopropyl ether solution. The precipitated copolymer was collected by filtration and washed twice with 300 g of hexane. The copolymer was dissolved in 180 g of tetrahydrofuran and 60 g of methanol, and 24.4 g of ethanolamine was added to the solution, which was stirred for 3 hours under reflux. The reaction solution was concentrated under reduced pressure. The concentrate was dissolved in ethyl acetate, followed by neutralization, separatory operation, and crystallization. There was obtained 71 g of Polymer 16.

Table 1 shows the proportion (in molar ratio) of units incorporated in these polymers, and Tables 2 to 4 show the structure of recurring units.

TABLE 1

| | Unit 1 | Proportion (mol %) | Unit 2 | Proportion (mol %) | Unit 3 | Proportion (Mol %) |
|---|---|---|---|---|---|---|
| Polymer 1 | A-1 | 70.0 | B-1 | 20.0 | C-1 | 10.0 |
| Polymer 2 | A-1 | 78.0 | B-3 | 12.0 | C-1 | 10.0 |
| Polymer 3 | A-1 | 79.0 | B-5 | 11.0 | C-1 | 10.0 |
| Polymer 4 | A-2 | 67.0 | B-2 | 23.0 | C-1 | 10.0 |
| Polymer 5 | A-2 | 76.0 | B-4 | 14.0 | C-1 | 10.0 |
| Polymer 6 | A-2 | 77.0 | B-6 | 13.0 | C-1 | 10.0 |
| Polymer 7 | A-1 | 68.0 | B-1 | 22.0 | C-2 | 10.0 |
| Polymer 8 | A-1 | 76.0 | B-3 | 14.0 | C-2 | 10.0 |
| Polymer 9 | A-1 | 77.0 | B-5 | 13.0 | C-2 | 10.0 |
| Polymer 10 | A-2 | 64.0 | B-2 | 26.0 | C-2 | 10.0 |
| Polymer 11 | A-2 | 73.0 | B-4 | 17.0 | C-2 | 10.0 |
| Polymer 12 | A-2 | 74.0 | B-6 | 16.0 | C-2 | 10.0 |
| Polymer 13 | A-2 | 46.0 | B-7 | 19.0 | C-3 | 35.0 |
| Polymer 14 | A-2 | 50.0 | B-8 | 15.0 | C-3 | 35.0 |
| Polymer 15 | A-2 | 50.0 | B-9 | 15.0 | C-3 | 35.0 |
| Polymer 16 | A-1 | 67.0 | B-10 | 23.0 | C-1 | 10.0 |

TABLE 2

A-1

[structure: 4-hydroxystyrene unit]

TABLE 2-continued
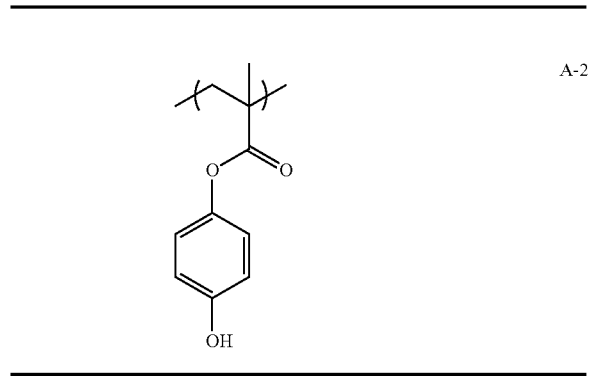
TABLE 3
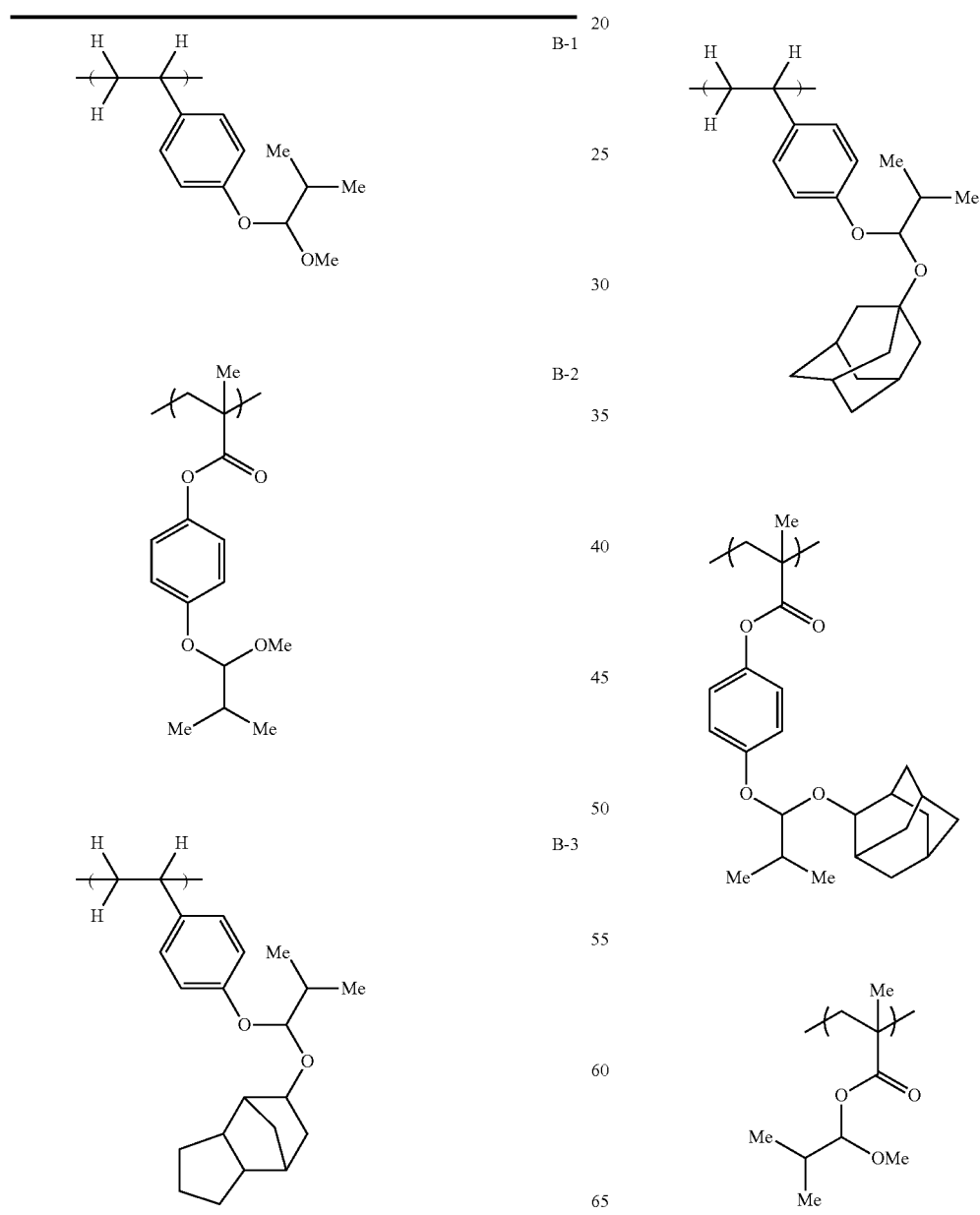
TABLE 3-continued
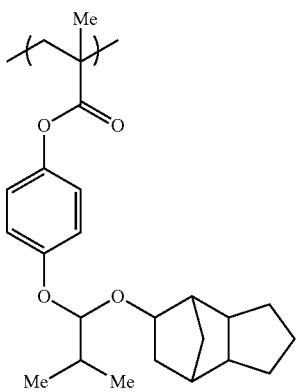

TABLE 3-continued

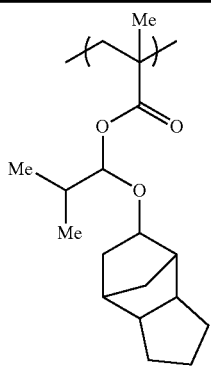
B-8

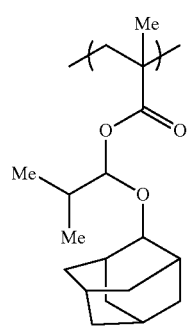
B-9

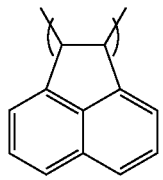
B-10

TABLE 4

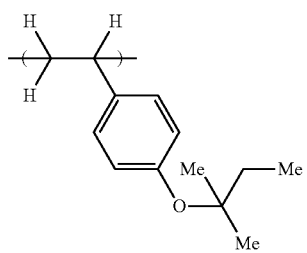 [SMILES: CCC(C)c1ccc(OC(C)(C)CC)cc1]
C-1

TABLE 4-continued

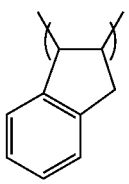
C-2

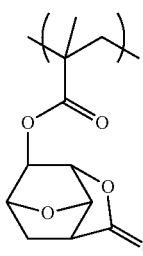
C-3

Preparation of Positive Resist Composition

A positive resist composition in solution form was prepared by dissolving each polymer (Polymers 1 to 16 synthesized above), a photoacid generator and basic compound in an organic solvent in accordance with the recipe shown in Table 6, and filtering through a filter with a pore size of 0.2 μm or a nylon or UPE filter with a pore size of 0.02 μm. The basic compound used is Base-1 of the structure shown below. The photoacid generator used is of the structure shown in Tables 5 and 6. The organic solvents in Table 7 are PGMEA (propylene glycol monomethyl ether acetate), EL (ethyl lactate), CyH (cyclohexanone), and PGME (propylene glycol monomethyl ether). The composition contained 0.075 part of surfactant PF-636 (Omnova Solutions Inc.).

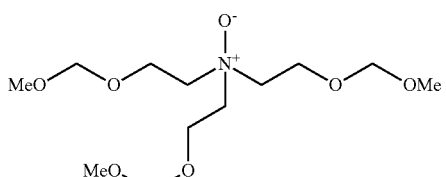
(Base-1)

TABLE 5

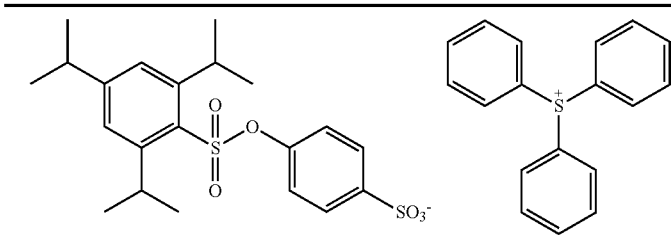
PAG-1

TABLE 5-continued
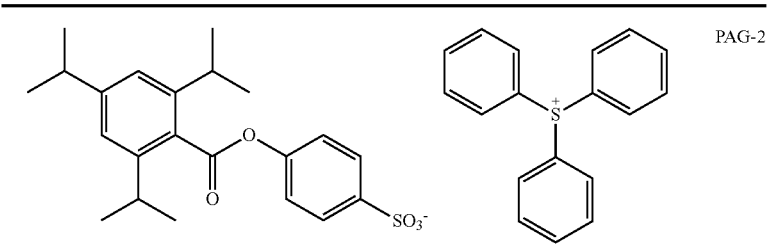
PAG-2
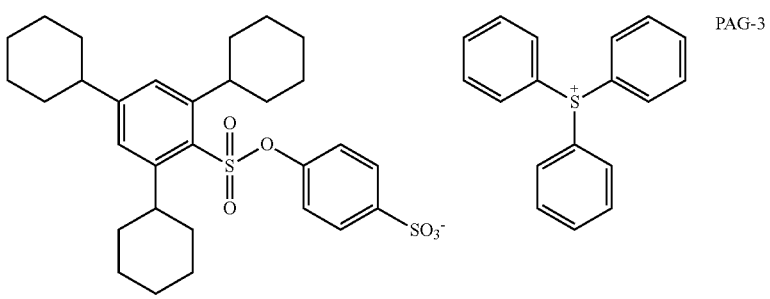
PAG-3
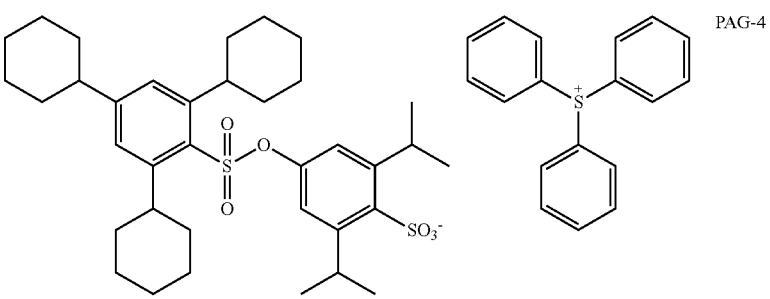
PAG-4
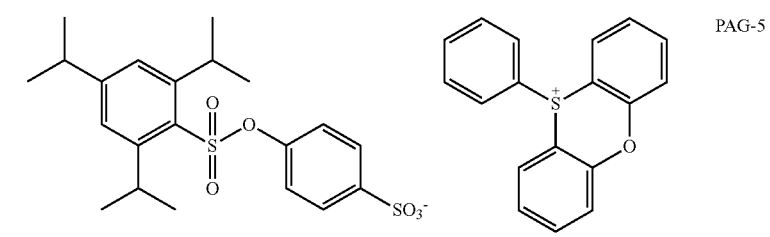
PAG-5
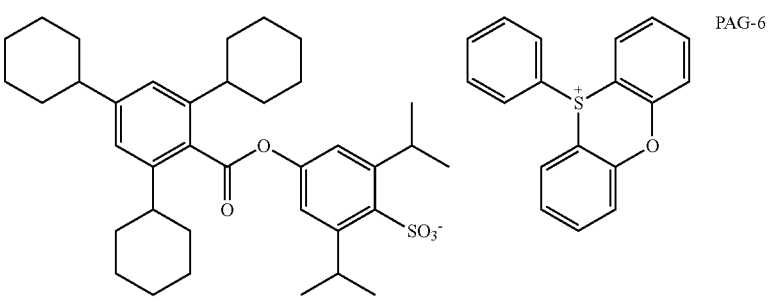
PAG-6

TABLE 5-continued
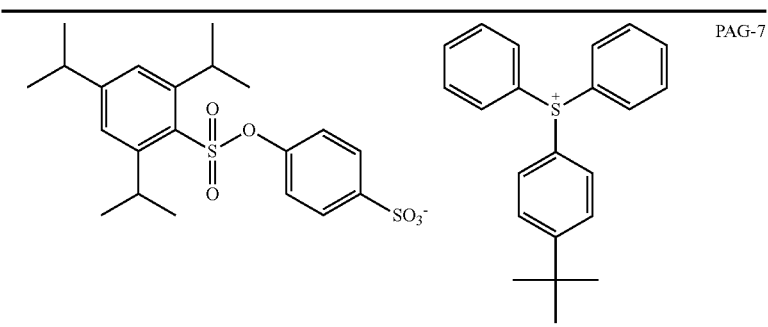
PAG-7
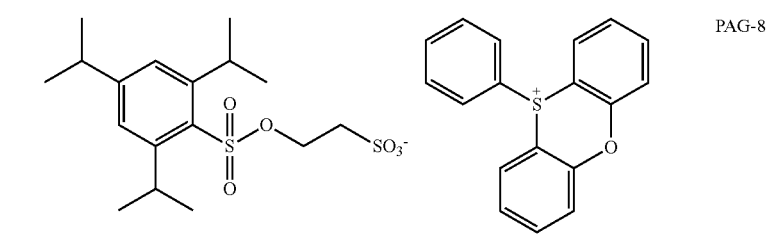
PAG-8
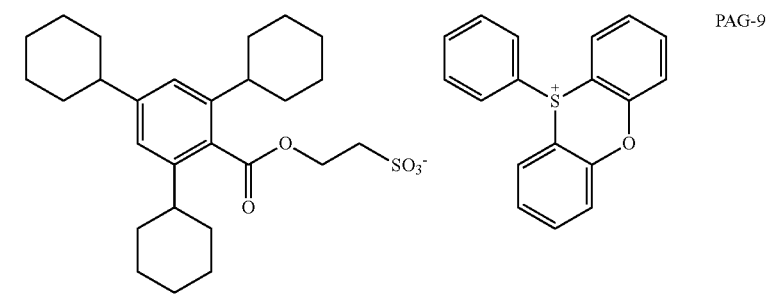
PAG-9
TABLE 6
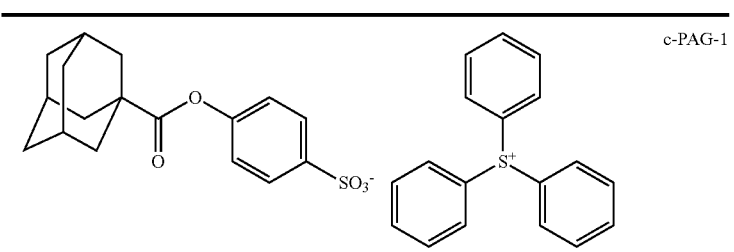
c-PAG-1
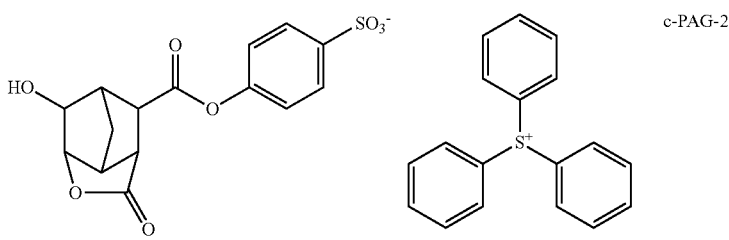
c-PAG-2

TABLE 6-continued

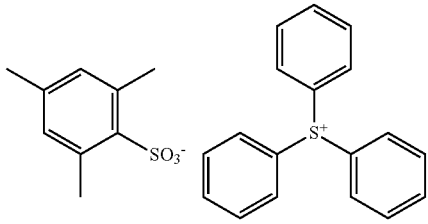

c-PAG-3

TABLE 7

| | | Photoacid generator (pbw) | Resin (pbw) | Base (pbw) | Solvent 1 (pbw) | Solvent 2 (pbw) | Solvent 3 (pbw) |
|---|---|---|---|---|---|---|---|
| Example | 1 | PAG-1(8) | Polymer 1(80) | Base-1(0.97) | PGMEA(1,000) | EL(1,000) | PGME(1,300) |
| | 2 | PAG-1(8) | Polymer 2(80) | Base-1(0.97) | PGMEA(1,000) | EL(1,000) | PGME(1,300) |
| | 3 | PAG-1(8) | Polymer 3(80) | Base-1(0.97) | PGMEA(1,000) | EL(1,000) | PGME(1,300) |
| | 4 | PAG-1(8) | Polymer 4(80) | Base-1(0.97) | PGMEA(1,000) | EL(1,000) | PGME(1,300) |
| | 5 | PAG-1(8) | Polymer 5(80) | Base-1(0.97) | PGMEA(1,000) | EL(1,000) | PGME(1,300) |
| | 6 | PAG-1(8) | Polymer 6(80) | Base-1(0.97) | PGMEA(1,000) | EL(1,000) | PGME(1,300) |
| | 7 | PAG-1(8) | Polymer 7(80) | Base-1(0.97) | PGMEA(1,000) | EL(1,000) | PGME(1,300) |
| | 8 | PAG-1(8) | Polymer 8(80) | Base-1(0.97) | PGMEA(1,000) | EL(1,000) | PGME(1,300) |
| | 9 | PAG-1(8) | Polymer 9(80) | Base-1(0.97) | PGMEA(1,000) | EL(1,000) | PGME(1,300) |
| | 10 | PAG-1(8) | Polymer 10(80) | Base-1(0.97) | PGMEA(1,000) | EL(1,000) | PGME(1,300) |
| | 11 | PAG-1(8) | Polymer 11(80) | Base-1(0.97) | PGMEA(1,000) | EL(1,000) | PGME(1,300) |
| | 12 | PAG-1(8) | Polymer 12(80) | Base-1(0.97) | PGMEA(1,000) | EL(1,000) | PGME(1,300) |
| | 13 | PAG-2(8) | Polymer 2(80) | Base-1(0.97) | PGMEA(1,000) | EL(1,000) | PGME(1,300) |
| | 14 | PAG-2(8) | Polymer 3(80) | Base-1(0.97) | PGMEA(1,000) | EL(1,000) | PGME(1,300) |
| | 15 | PAG-3(8) | Polymer 2(80) | Base-1(0.97) | PGMEA(1,000) | EL(1,000) | PGME(1,300) |
| | 16 | PAG-3(8) | Polymer 3(80) | Base-1(0.97) | PGMEA(1,000) | EL(1,000) | PGME(1,300) |
| | 17 | PAG-4(8) | Polymer 2(80) | Base-1(0.97) | PGMEA(1,000) | EL(1,000) | PGME(1,300) |
| | 18 | PAG-4(8) | Polymer 3(80) | Base-1(0.97) | PGMEA(1,000) | EL(1,000) | PGME(1,300) |
| | 19 | PAG-5(8) | Polymer 2(80) | Base-1(0.97) | PGMEA(1,000) | EL(1,000) | PGME(1,300) |
| | 20 | PAG-5(8) | Polymer 3(80) | Base-1(0.97) | PGMEA(1,000) | EL(1,000) | PGME(1,300) |
| | 21 | PAG-6(8) | Polymer 2(80) | Base-1(0.97) | PGMEA(1,000) | EL(1,000) | PGME(1,300) |
| | 22 | PAG-6(8) | Polymer 3(80) | Base-1(0.97) | PGMEA(1,000) | EL(1,000) | PGME(1,300) |
| | 23 | PAG-7(8) | Polymer 2(80) | Base-1(0.97) | PGMEA(1,000) | EL(1,000) | PGME(1,300) |
| | 24 | PAG-7(8) | Polymer 3(80) | Base-1(0.97) | PGMEA(1,000) | EL(1,000) | PGME(1,300) |
| | 25 | PAG-1(8) | Polymer 8(80) | Base-1(0.97) | PGMEA(1,000) | EL(1,000) | PGME(1,300) |
| | 26 | PAG-2(8) | Polymer 8(80) | Base-1(0.97) | PGMEA(1,000) | EL(1,000) | PGME(1,300) |
| | 27 | PAG-3(8) | Polymer 8(80) | Base-1(0.97) | PGMEA(1,000) | EL(1,000) | PGME(1,300) |
| | 28 | PAG-4(8) | Polymer 8(80) | Base-1(0.97) | PGMEA(1,000) | EL(1,000) | PGME(1,300) |
| | 29 | PAG-5(8) | Polymer 8(80) | Base-1(0.97) | PGMEA(1,000) | EL(1,000) | PGME(1,300) |
| | 30 | PAG-6(8) | Polymer 8(80) | Base-1(0.97) | PGMEA(1,000) | EL(1,000) | PGME(1,300) |
| | 31 | PAG-7(8) | Polymer 8(80) | Base-1(0.97) | PGMEA(1,000) | EL(1,000) | PGME(1,300) |
| | 32 | PAG-8(8) | Polymer 8(80) | Base-1(0.97) | PGMEA(1,000) | EL(1,000) | PGME(1,300) |
| | 33 | PAG-9(8) | Polymer 8(80) | Base-1(0.97) | PGMEA(1,000) | EL(1,000) | PGME(1,300) |
| | 34 | PAG-1(8) | Polymer 13(80) | Base-1(0.97) | PGMEA(800) | CyH(1,600) | PGME(400) |
| | 35 | PAG-1(8) | Polymer 14(80) | Base-1(0.97) | PGMEA(800) | CyH(1,600) | PGME(400) |
| | 36 | PAG-1(8) | Polymer 15(80) | Base-1(0.97) | PGMEA(800) | CyH(1,600) | PGME(400) |
| | 37 | PAG-1(8) | Polymer 16(80) | Base-1(0.97) | PGMEA(1,000) | EL(1,000) | PGME(1,300) |
| Comparative Example | 1 | c-PAG-1(8) | Polymer 2(80) | Base-1(0.97) | PGMEA(1,000) | EL(1,000) | PGME(1,300) |
| | 2 | c-PAG-1(8) | Polymer 3(80) | Base-1(0.97) | PGMEA(1,000) | EL(1,000) | PGME(1,300) |
| | 3 | c-PAG-2(8) | Polymer 2(80) | Base-1(0.97) | PGMEA(1,000) | EL(1,000) | PGME(1,300) |
| | 4 | c-PAG-2(8) | Polymer 3(80) | Base-1(0.97) | PGMEA(1,000) | EL(1,000) | PGME(1,300) |
| | 5 | c-PAG-3(8) | Polymer 2(80) | Base-1(0.97) | PGMEA(1,000) | EL(1,000) | PGME(1,300) |
| | 6 | c-PAG-3(8) | Polymer 3(80) | Base-1(0.97) | PGMEA(1,000) | EL(1,000) | PGME(1,300) |
| | 7 | c-PAG-1(8) | Polymer 13(80) | Base-1(0.97) | PGMEA(800) | CyH(1,600) | PGME(400) |

Examples 1 to 33, 37 and Comparative Examples 1 to 6

EB Writing Test 1

Using a coater/developer system ACT-M (Tokyo Electron Ltd.), each of the positive resist compositions (prepared above as Examples 1 to 33, 37 and Comparative Examples 1 to 6) was spin coated onto a mask blank of 152 mm squares having a chromium oxynitride film at the outermost surface and prebaked on a hot plate at 90° C. for 600 seconds to form a resist film of 90 nm thick. The thickness of the resist film was measured by an optical film thickness measurement system Nanospec (Nanometrics Inc.). Measurement was made at 81 points in the plane of the blank substrate excluding a peripheral band extending 10 mm inward from the blank periphery, and an average film thickness and a film thickness range were computed therefrom.

The coated mask blanks were exposed to electron beam using an EB writer system EBM-5000Plus (NuFlare Technology Inc., accelerating voltage 50 keV), then baked (PEB)

at 120° C. for 600 seconds, and developed in a 2.38 wt % tetramethylammonium hydroxide (TMAH) aqueous solution, thereby yielding positive patterns.

The patterned mask blank was observed under a top-down scanning electron microscope (TDSEM). The optimum exposure (Eop) was defined as the exposure dose ($\mu C/cm^2$) which provided a 1:1 resolution at the top and bottom of a 400-nm 1:1 line-and-space (LS) pattern. The maximum resolution of the resist was defined as the minimum line width of a LS pattern that could be resolved at the optimum exposure. The LER of a 200-nm LS pattern was measured under SEM. On observation in cross section of the resist pattern under SEM, it was visually judged whether or not the pattern profile was rectangular.

For evaluation of CDU, the line width of the pattern at the optimum exposure Eop ($\mu C/cm^2$) (which provided a 1:1 resolution of a 400-nm 1:1 LS pattern) was measured at 49 points in the plane of the blank substrate excluding a peripheral band extending 20 mm inward from the blank periphery. A $3\sigma$ value was computed by subtracting the width at each measurement point from the average line width, and reported as CDU.

Table 8 tabulates the test results of the inventive and comparative resist compositions on EB image writing.

TABLE 8

| | | Eop, $\mu C/cm^2$ | Maximum resolution, nm | LER, nm | CDU ($3\sigma$), nm | Pattern profile |
|---|---|---|---|---|---|---|
| Example | 1 | 21 | 45 | 4.7 | 2.2 | rectangular |
| | 2 | 22 | 40 | 4.6 | 2.3 | rectangular |
| | 3 | 24 | 40 | 4.6 | 2.2 | rectangular |
| | 4 | 23 | 45 | 4.6 | 2.1 | rectangular |
| | 5 | 25 | 45 | 4.9 | 2.3 | rectangular |
| | 6 | 24 | 40 | 4.4 | 2.2 | rectangular |
| | 7 | 23 | 40 | 5.0 | 2.2 | rectangular |
| | 8 | 23 | 45 | 4.7 | 2.4 | rectangular |
| | 9 | 25 | 45 | 4.6 | 2.2 | rectangular |
| | 10 | 22 | 45 | 4.8 | 2.2 | rectangular |
| | 11 | 23 | 45 | 4.8 | 2.3 | rectangular |
| | 12 | 21 | 45 | 4.7 | 2.1 | rectangular |
| | 13 | 24 | 40 | 4.6 | 2.2 | rectangular |
| | 14 | 25 | 40 | 4.8 | 2.2 | rectangular |
| | 15 | 23 | 40 | 4.7 | 2.3 | rectangular |
| | 16 | 22 | 40 | 4.8 | 2.4 | rectangular |
| | 17 | 21 | 40 | 4.5 | 2.2 | rectangular |
| | 18 | 21 | 40 | 4.6 | 2.3 | rectangular |
| | 19 | 24 | 45 | 4.6 | 2.5 | rectangular |
| | 20 | 25 | 45 | 4.8 | 2.4 | rectangular |
| | 21 | 23 | 40 | 4.9 | 2.3 | rectangular |
| | 22 | 24 | 40 | 4.8 | 2.2 | rectangular |
| | 23 | 25 | 45 | 4.8 | 2.3 | rectangular |
| | 24 | 24 | 45 | 4.8 | 2.2 | rectangular |
| | 25 | 25 | 45 | 4.7 | 2.5 | rectangular |
| | 26 | 24 | 45 | 4.8 | 2.3 | rectangular |
| | 27 | 23 | 45 | 4.6 | 2.4 | rectangular |
| | 28 | 25 | 45 | 4.7 | 2.5 | rectangular |
| | 29 | 26 | 45 | 4.7 | 2.4 | rectangular |
| | 30 | 24 | 45 | 4.7 | 2.4 | rectangular |
| | 31 | 24 | 45 | 5.0 | 2.6 | rectangular |
| | 32 | 25 | 45 | 5.0 | 2.7 | rectangular |
| | 33 | 25 | 45 | 5.0 | 2.6 | rectangular |
| | 37 | 36 | 40 | 4.6 | 2.3 | rectangular |
| Comparative Example | 1 | 24 | 55 | 7.2 | 3.4 | rectangular |
| | 2 | 23 | 55 | 6.9 | 3.5 | rectangular |
| | 3 | 25 | 55 | 8.3 | 3.6 | rectangular |
| | 4 | 26 | 55 | 8.4 | 3.6 | rectangular |
| | 5 | 25 | 55 | 7.6 | 3.5 | rectangular |
| | 6 | 22 | 55 | 7.8 | 3.6 | rectangular |

Examples 34 to 36 and Comparative Example 7

EUV Exposure Test 1

Each of the positive resist compositions (prepared above as Examples 34 to 36 and Comparative Example 7) was spin coated on a silicon substrate (diameter 4 inches, vapor primed with hexamethyldisilazane (HMDS)) and prebaked on a hot plate at 105° C. for 60 seconds to form a resist film of 50 nm thick. EUV exposure was performed by dipole illumination at NA 0.3. Immediately after the exposure, the resist film was baked (PEB) on a hot plate for 60 seconds and puddle developed in a 2.38 wt % TMAH aqueous solution for 30 seconds to form a positive pattern.

The optimum exposure (Eop) is defined as the exposure dose that provides a 1:1 resolution of a 35-nm line-and-space pattern. Maximum resolution is a minimum size that can be resolved at Eop. The 35-nm LS pattern was measured for LER under SEM. On observation in cross section of the resist pattern under SEM, it was visually judged whether or not the pattern profile was rectangular.

The results of the resist compositions by EUV lithography test are shown in Table 9.

TABLE 9

| | Eop, $mJ/cm^2$ | Maximum resolution, nm | LER, nm | Pattern profile |
|---|---|---|---|---|
| Example 34 | 15 | 28 | 4.0 | rectangular |
| Example 35 | 14 | 26 | 4.1 | rectangular |
| Example 36 | 15 | 28 | 4.1 | rectangular |
| Comparative Example 7 | 12 | 50 | 9.6 | rectangular |

As seen from the results in Tables 8 and 9, the positive resist compositions containing the sulfonium salt of formula (1) within the scope of the invention (Examples 1 to 33, 37 or Examples 34 to 36) exhibit a high resolution, satisfactory pattern rectangularity, and acceptable values of CDU and LER. In contrast, the resist compositions containing a sulfonium salt which is less bulky than the sulfonium salt of formula (1) (Comparative Examples 1 to 6 or Comparative Example 7) are inferior in resolution, CDU, and LER. This is because the sulfonium salts used in Comparative Examples are less bulky than the sulfonium salts of formula (1) and fail in effective control of acid diffusion.

Synthesis Example 3

Synthesis of Negative Resist Polymers

Polymers for use in negative resist compositions were synthesized according to the following formulation. The compositional proportion (in molar ratio) of polymers is shown in Table 10. The structure of recurring units is shown in Tables 11 to 13.

Synthesis Example 3-1

Synthesis of Polymer 17

A 3-L flask was charged with 238.0 g of acetoxystyrene, 22.6 g of 4-chlorostyrene, 189.4 g of indene, and 675 g of toluene as a solvent. The reactor was cooled to −70° C. in a nitrogen blanket, followed by three repeated cycles of vacuum evacuation and nitrogen flow. The reactor was warmed to room temperature, fed with 40.5 g of 2,2'-azobis (2,4-dimethylvaleronitrile) (V-65, Wako Pure Chemical Industries, Ltd.) as a polymerization initiator, and heated at 45° C. whereupon reaction took place for 20 hours. The temperature was then raised to 55° C. whereupon reaction took place for a further 20 hours. The reaction solution was concentrated to a half volume and precipitated in 15.0 L of methanol. The resulting white solids were collected by filtration and dried in vacuum at 40° C., yielding 311 g of a white polymer.

The polymer was dissolved again in 488 g of methanol and 540 g of tetrahydrofuran, whereupon 162 g of triethylamine and 32 g of water were added to the polymer solution. Deprotection reaction occurred at 60° C. for 40 hours. Then for fractionation, the reaction solution was concentrated and dissolved in a mixture of 548 g of methanol and 112 g of acetone. To this solution, 990 g of hexane was added dropwise over 10 minutes. The mixed white turbid solution was left at rest for separation, whereupon the lower (polymer) layer was taken out and concentrated. The polymer concentrate was dissolved again in a mixture of 548 g of methanol and 112 g of acetone, after which the solution was combined with 990 g of hexane for dispersion and separation. The lower (polymer) layer was taken out and concentrated. The concentrate was dissolved in 870 g of ethyl acetate, followed by one cycle of neutralization, separation and washing with a mixture of 250 g of water and 98 g of acetic acid, one cycle of separation and washing with 225 g of water and 75 g of pyridine, and four cycles of separation and washing with 225 g of water. Thereafter, the upper layer, ethyl acetate solution was concentrated, dissolved in 250 g of acetone, precipitated in 15 L of water, filtered, and vacuum dried at 50° C. for 40 hours, yielding 187 g of a white polymer.

The polymer, designated Polymer 17, was analyzed by $^{13}$C-NMR, $^1$H-NMR and GPC, from which the composition and molecular weight were determined.
Copolymer Compositional Ratio (Molar Ratio)
hydroxystyrene/4-chlorostyrene/indene=78.0/11.0/11.0
Mw=4,500
Dispersity Mw/Mn=1.65

Synthesis Example 3-2

Synthesis of Polymer 18

In nitrogen atmosphere, 380.0 g of 4-acetoxystyrene, 70.0 g of 4-chlorostyrene, 50.1 g of acenaphthylene, 59 g of dimethyl 2,2'-azobis(2-methylpropionate) (V-601 by Wako Pure Chemical Industries, Ltd.), and 900 g of toluene were fed into a 3-L dropping cylinder to form a monomer solution. A 3-L flask in nitrogen atmosphere was charged with 300 g of toluene, which was heated at 80° C. with stirring. With stirring, the monomer solution was added dropwise to the flask over 4 hours. After the completion of dropwise addition, the polymerization solution was continuously stirred for 18 hours while maintaining its temperature at 80° C. The polymerization solution was cooled to room temperature, whereupon it was added dropwise to 10 kg of hexane. The copolymer precipitated was collected by filtration and washed twice with 2,000 g of a 10:1 mixture of hexane and toluene. In the flask in nitrogen atmosphere, the copolymer was dissolved in a mixture of 1,260 g of tetrahydrofuran and 420 g of methanol, and 180 g of ethanolamine was added to the polymer solution, which was stirred at 60° C. for 3 hours. The reaction solution was concentrated under reduced pressure. The concentrate was dissolved in a mixture of 3,000 g of ethyl acetate and 800 g of water. The solution was transferred to a separatory funnel. With 90 g of acetic acid added, separatory operation was carried out. The lower layer was distilled off. To the organic layer, 800 g of water and 121 g of pyridine were added, followed by separatory operation. The lower layer was distilled off. To the organic layer, 800 g of water was added, followed by water washing and separatory operation (totaling to 5 cycles of water washing and separatory operation). Phase separation was promoted by adding 150 g of acetone and stirring for some time in the resting step of each separatory operation.

The organic layer after the separation was concentrated and dissolved in 1,200 g of acetone. The acetone solution was passed through a nylon filter with a pore size of 0.02 μm and added dropwise to 10 L of water whereupon crystals precipitated. The precipitate was filtered, washed with water, and suction filtered for 2 hours. The filter cake was dissolved in 1,200 g of acetone again. The acetone solution was passed through a nylon filter with a pore size of 0.02 μm and added dropwise to 10 L of water whereupon crystals precipitated. The precipitate was filtered, washed with water, and dried, obtaining 400 g of a white polymer.

The polymer, designated Polymer 18, was analyzed by $^{13}$C-NMR and GPC, from which the composition and molecular weight were determined.
Copolymer Compositional Ratio (Molar Ratio)
hydroxystyrene/4-chlorostyrene/acenaphthylene=75.0/15.0/10.0
Mw=4,100
Dispersity Mw/Mn=1.72

Synthesis Examples 3-3 to 3-10

Synthesis of Polymers 19 to 26

Polymers in Table 10 were synthesized by the same procedure as in Synthesis Examples 3-1 and 3-2 aside from changing the type and amount of monomers. Table 10 shows the proportion (in molar ratio) of units incorporated in these polymers, and Tables 11 to 13 show the structure of recurring units.

Synthesis Example 3-11

Synthesis of Polymer 27

In nitrogen atmosphere, 64.7 g of 4-hydroxyphenyl methacrylate, 30.7 g of indene, 4.6 g of 4-chlorostyrene, 12.2 g of dimethyl 2,2'-azobis(2-methylpropionate) (V-601), and 150 g of methyl ethyl ketone were fed into a dropping cylinder to form a monomer solution. A flask in nitrogen atmosphere was charged with 75 g of methyl ethyl ketone, which was heated at 80° C. with stirring. With stirring, the monomer solution was added dropwise to the flask over 4 hours. After the completion of dropwise addition, the polymerization solution was continuously stirred for 18 hours while maintaining its temperature at 80° C. The polymerization solution was cooled to room temperature, whereupon it was added dropwise to 1.5 kg of hexane/diisopropyl ether. The copolymer precipitated was collected by filtration and washed twice with 300 g of hexane.

The polymer, designated Polymer 27, was analyzed by $^{13}$C-NMR and GPC, from which the composition and molecular weight were determined.
Copolymer Compositional Ratio (Molar Ratio)
4-hydroxyphenyl methacrylate/4-chlorostyrene/indene=68.0/22.0/10.0
Mw=4,100
Dispersity Mw/Mn=1.72

Synthesis Examples 3-12 to 3-15

Synthesis of Polymers 28 to 31

Polymers in Table 10 were synthesized by the same procedure as in Synthesis Example 3-11 aside from changing the type and amount of monomers. Table 10 shows the proportion (in molar ratio) of units incorporated in these polymers, and Tables 11 to 13 show the structure of recurring units.

TABLE 10

|  | Unit 1 | Proportion (mol %) | Unit 2 | Proportion (mol %) | Unit 3 | Proportion (mol %) |
|---|---|---|---|---|---|---|
| Polymer 17 | D-1 | 78.0 | E-1 | 11.0 | F-1 | 11.0 |
| Polymer 18 | D-1 | 75.0 | E-1 | 15.0 | F-2 | 10.0 |
| Polymer 19 | D-1 | 74.0 | E-2 | 15.0 | F-1 | 11.0 |
| Polymer 20 | D-1 | 76.0 | E-2 | 14.0 | F-2 | 10.0 |
| Polymer 21 | D-1 | 75.0 | E-3 | 15.0 | F-1 | 10.0 |
| Polymer 22 | D-1 | 77.0 | E-3 | 12.0 | F-2 | 11.0 |
| polymer 23 | D-1 | 74.0 | E-4 | 14.0 | F-1 | 12.0 |
| Polymer 24 | D-1 | 77.0 | E-4 | 13.0 | F-2 | 10.0 |
| Polymer 25 | D-1 | 57.0 | E-5 | 33.0 | F-1 | 10.0 |
| Polymer 26 | D-1 | 60.0 | E-5 | 30.0 | F-2 | 10.0 |
| Polymer 27 | D-2 | 68.0 | E-1 | 22.0 | F-1 | 10.0 |
| Polymer 28 | D-2 | 67.0 | E-2 | 23.0 | F-2 | 10.0 |
| Polymer 29 | D-2 | 50.0 | E-1 | 15.0 | F-3 | 35.0 |
| Polymer 30 | D-2 | 48.0 | E-2 | 17.0 | F-3 | 35.0 |
| Polymer 31 | D-2 | 49.0 | E-5 | 16.0 | F-3 | 35.0 |

TABLE 11

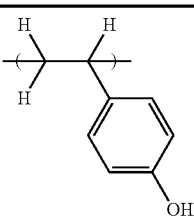
D-1

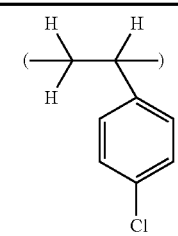
D-2

TABLE 12

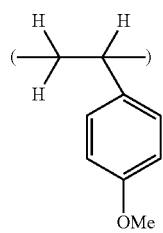
E-1

TABLE 12-continued

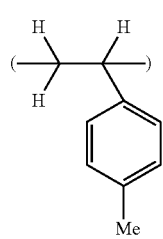
E-2

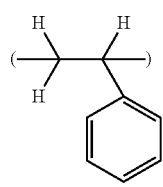
E-3

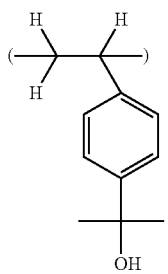
E-4

E-5

TABLE 13

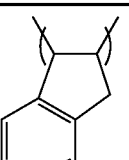
F-1

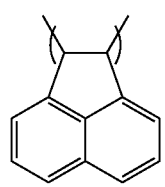
F-2

TABLE 13-continued

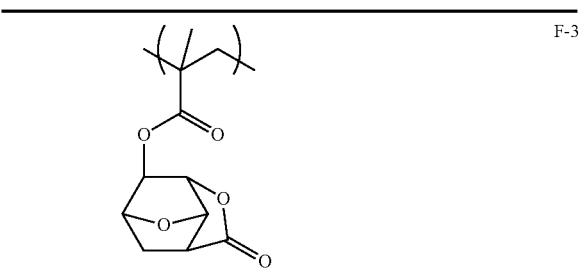

F-3

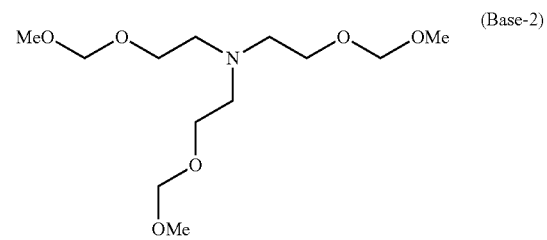 [SMILES: COCOCCN(CCOCOC)CCOCOC]

(Base-2)

Preparation of Negative Resist Composition

A negative resist composition in solution form was prepared by dissolving each polymer (Polymers 17 to 31 synthesized above), a photoacid generator, basic compound and crosslinker in an organic solvent in accordance with the recipe shown in Table 14, and filtering through a filter with a pore size of 0.2 μm or a nylon or UPE filter with a pore size of 0.02 μm. The basic compound used is Base-2 of the structure shown below.

The photoacid generator used is of the structure shown in Tables 5 and 6. The crosslinker is TMGU (tetramethoxymethyl glycoluril). The organic solvents in Table 14 are PGMEA (propylene glycol monomethyl ether acetate), EL (ethyl lactate), CyH (cyclohexanone), and PGME (propylene glycol monomethyl ether). The composition contained 0.075 part of surfactant PF-636 (Omnova Solutions Inc.).

TABLE 14

|  |  | Photoacid generator (pbw) | Resin (pbw) | Base (pbw) | Crosslinker (pbw) | Solvent 1 (pbw) | Solvent 2 (pbw) | Solvent 3 (pbw) |
|---|---|---|---|---|---|---|---|---|
| Example | 38 | PAG-1(8) | Polymer 17(80) | Base-2(1.1) | TMGU(8.2) | PGMEA(940) | EL(2,170) | — |
|  | 39 | PAG-1(8) | Polymer 18(80) | Base-2(1.1) | TMGU(8.2) | PGMEA(940) | EL(2,170) | — |
|  | 40 | PAG-1(8) | Polymer 19(80) | Base-2(1.1) | TMGU(8.2) | PGMEA(940) | EL(2,170) | — |
|  | 41 | PAG-1(8) | Polymer 20(80) | Base-2(1.1) | TMGU(8.2) | PGMEA(940) | EL(2,170) | — |
|  | 42 | PAG-1(8) | Polymer 21(80) | Base-2(1.1) | TMGU(8.2) | PGMEA(940) | EL(2,170) | — |
|  | 43 | PAG-1(8) | Polymer 22(80) | Base-2(1.1) | TMGU(8.2) | PGMEA(940) | EL(2,170) | — |
|  | 44 | PAG-1(8) | Polymer 23(80) | Base-2(1.1) | TMGU(8.2) | PGMEA(940) | EL(2,170) | — |
|  | 45 | PAG-1(8) | Polymer 24(80) | Base-2(1.1) | TMGU(8.2) | PGMEA(940) | EL(2,170) | — |
|  | 46 | PAG-1(8) | Polymer 25(80) | Base-2(1.0) | — | PGMEA(940) | EL(2,170) | — |
|  | 47 | PAG-1(8) | Polymer 26(80) | Base-2(1.0) | — | PGMEA(940) | EL(2,170) | — |
|  | 48 | PAG-1(8) | Polymer 27(80) | Base-2(1.1) | TMGU(8.2) | PGMEA(940) | EL(2,170) | — |
|  | 49 | PAG-1(8) | Polymer 28(80) | Base-2(1.1) | TMGU(8.2) | PGMEA(940) | EL(2,170) | — |
|  | 50 | PAG-1(8) | Polymer 29(80) | Base-2(1.1) | TMGU(8.2) | PGMEA(940) | EL(2,170) | — |
|  | 51 | PAG-1(8) | Polymer 30(80) | Base-2(1.1) | TMGU(8.2) | PGMEA(940) | EL(2,170) | — |
|  | 52 | PAG-1(8) | Polymer 31(80) | Base-2(1.0) | — | PGMEA(940) | EL(2,170) | — |
|  | 53 | PAG-2(8) | Polymer 17(80) | Base-2(1.1) | TMGU(8.2) | PGMEA(940) | EL(2,170) | — |
|  | 54 | PAG-2(8) | Polymer 26(80) | Base-2(1.0) | — | PGMEA(940) | EL(2,170) | — |
|  | 55 | PAG-3(8) | Polymer 17(80) | Base-2(1.1) | TMGU(8.2) | PGMEA(940) | EL(2,170) | — |
|  | 56 | PAG-3(8) | Polymer 26(80) | Base-2(1.0) | — | PGMEA(940) | EL(2,170) | — |
|  | 57 | PAG-4(8) | Polymer 17(80) | Base-2(1.1) | TMGU(8.2) | PGMEA(940) | EL(2,170) | — |
|  | 58 | PAG-4(8) | Polymer 26(80) | Base-2(1.0) | — | PGMEA(940) | EL(2,170) | — |
|  | 59 | PAG-5(8) | Polymer 17(80) | Base-2(1.1) | TMGU(8.2) | PGMEA(940) | EL(2,170) | — |
|  | 60 | PAG-5(8) | Polymer 26(80) | Base-2(1.0) | — | PGMEA(940) | EL(2,170) | — |
|  | 61 | PAG-6(8) | Polymer 17(80) | Base-2(1.1) | TMGU(8.2) | PGMEA(940) | EL(2,170) | — |
|  | 62 | PAG-6(8) | Polymer 26(80) | Base-2(1.0) | — | PGMEA(940) | EL(2,170) | — |
|  | 63 | PAG-7(8) | Polymer 17(80) | Base-2(1.1) | TMGU(8.2) | PGMEA(940) | EL(2,170) | — |
|  | 64 | PAG-7(8) | Polymer 26(80) | Base-2(1.0) | — | PGMEA(940) | EL(2,170) | — |
|  | 65 | PAG-8(8) | Polymer 17(80) | Base-2(1.1) | TMGU(8.2) | PGMEA(940) | EL(2,170) | — |
|  | 66 | PAG-9(8) | Polymer 17(80) | Base-2(1.1) | TMGU(8.2) | PGMEA(940) | EL(2,170) | — |
|  | 67 | PAG-1(8) | Polymer 29(80) | Base-2(1.1) | TMGU(8.2) | PGMEA(800) | CyH(1,600) | PGME(400) |
|  | 68 | PAG-1(8) | Polymer 30(80) | Base-2(1.1) | TMGU(8.2) | PGMEA(800) | CyH(1,600) | PGME(400) |
|  | 69 | PAG-1(8) | Polymer 31(80) | Base-2(1.0) | — | PGMEA(800) | CyH(1,600) | PGME(400) |
| Comparative Example | 8 | c-PAG-1(8) | Polymer 17(80) | Base-2(1.1) | TMGU(8.2) | PGMEA(940) | EL(2,170) | — |
|  | 9 | c-PAG-2(8) | Polymer 17(80) | Base-2(1.1) | TMGU(8.2) | PGMEA(940) | EL(2,170) | — |
|  | 10 | c-PAG-3(8) | Polymer 17(80) | Base-2(1.1) | TMGU(8.2) | PGMEA(940) | EL(2,170) | — |
|  | 11 | c-PAG-1(8) | Polymer 26(80) | Base-2(1.0) | — | PGMEA(940) | EL(2,170) | — |
|  | 12 | c-PAG-1(8) | Polymer 17(80) | Base-2(1.1) | TMGU(8.2) | PGMEA(800) | CyH(1,600) | PGME(400) |
|  | 13 | c-PAG-1(8) | Polymer 26(80) | Base-2(1.0) | — | PGMEA(800) | CyH(1,600) | PGME(400) |

Examples 38 to 66 and Comparative Examples 8 to 11

EB Writing Test 2

Using a coater/developer system ACT-M (Tokyo Electron Ltd.), each of the negative resist compositions (prepared above as Examples 38 to 66 and Comparative Examples 8 to 11) was spin coated onto a mask blank of 152 mm squares having a chromium oxynitride film at the outermost surface and prebaked on a hot plate at 90° C. for 600 seconds to form a resist film of 90 nm thick. The thickness of the resist film was measured by an optical film thickness measurement system Nanospec (Nanometrics Inc.). Measurement was made at 81 points in the plane of the blank substrate excluding a peripheral band extending 10 mm inward from the blank periphery, and an average film thickness and a film thickness range were computed therefrom.

The coated mask blanks were exposed to electron beam using an EB writer system EBM-5000Plus (NuFlare Technology Inc., accelerating voltage 50 keV), then baked (PEB) at 120° C. for 600 seconds, and developed in a 2.38 wt % TMAH aqueous solution, thereby yielding negative patterns.

The patterned mask blank was observed under TDSEM. The optimum exposure (Eop) was defined as the exposure dose ($\mu C/cm^2$) which provided a 1:1 resolution at the top and bottom of a 400-nm 1:1 line-and-space (LS) pattern. The maximum resolution of the resist was defined as the minimum line width of an LS pattern that could be resolved at the optimum exposure. The LER of a 200-nm LS pattern was measured under SEM. On observation in cross section of the resist pattern under SEM, it was visually judged whether or not the pattern profile was rectangular.

For evaluation of CDU, the line width of the pattern at the optimum exposure Eop ($\mu C/cm^2$) (which provided a 1:1 resolution of a 400-nm 1:1 LS pattern) was measured at 49 points in the plane of the blank substrate excluding a peripheral band extending 20 mm inward from the blank periphery. A $3\sigma$ value was computed by subtracting the width at each measurement point from the average line width, and reported as CDU.

Table 15 tabulates the test results of the inventive and comparative resist compositions on EB image writing.

TABLE 15

| | | Eop (LS), $\mu C/cm^2$ | Maximum resolution, (LS), nm | Maximum resolution (IS), nm | LER, nm | CDU ($3\sigma$), nm | Pattern profile |
|---|---|---|---|---|---|---|---|
| Example | 38 | 25 | 40 | 40 | 4.6 | 2.3 | rectangular |
| | 39 | 24 | 40 | 45 | 4.8 | 2.2 | rectangular |
| | 40 | 23 | 45 | 40 | 4.7 | 2.1 | rectangular |
| | 41 | 25 | 40 | 40 | 4.7 | 2.4 | rectangular |
| | 42 | 26 | 40 | 45 | 4.8 | 2.5 | rectangular |
| | 43 | 24 | 45 | 40 | 4.8 | 2.4 | rectangular |
| | 44 | 25 | 40 | 40 | 4.5 | 2.2 | rectangular |
| | 45 | 25 | 45 | 40 | 4.5 | 2.5 | rectangular |
| | 46 | 24 | 45 | 40 | 4.5 | 2.4 | rectangular |
| | 47 | 25 | 40 | 40 | 4.9 | 2.3 | rectangular |
| | 48 | 26 | 40 | 45 | 4.8 | 2.2 | rectangular |
| | 49 | 24 | 45 | 40 | 4.9 | 2.3 | rectangular |
| | 50 | 25 | 40 | 40 | 4.9 | 2.4 | rectangular |
| | 51 | 25 | 40 | 45 | 4.8 | 2.2 | rectangular |
| | 52 | 26 | 45 | 40 | 4.8 | 2.3 | rectangular |
| | 53 | 24 | 40 | 40 | 4.8 | 2.3 | rectangular |
| | 54 | 25 | 40 | 45 | 4.8 | 2.4 | rectangular |
| | 55 | 26 | 40 | 40 | 4.6 | 2.3 | rectangular |
| | 56 | 24 | 45 | 40 | 4.7 | 2.4 | rectangular |
| | 57 | 25 | 40 | 45 | 4.9 | 2.4 | rectangular |
| | 58 | 25 | 45 | 40 | 4.6 | 2.5 | rectangular |
| | 59 | 25 | 45 | 45 | 4.5 | 2.3 | rectangular |
| | 60 | 25 | 40 | 40 | 4.8 | 2.4 | rectangular |
| | 61 | 26 | 45 | 40 | 4.8 | 2.4 | rectangular |
| | 62 | 25 | 45 | 45 | 4.7 | 2.3 | rectangular |
| | 63 | 26 | 40 | 40 | 4.6 | 2.5 | rectangular |
| | 64 | 24 | 40 | 40 | 4.8 | 2.4 | rectangular |
| | 65 | 26 | 45 | 45 | 4.9 | 2.5 | rectangular |
| | 66 | 25 | 45 | 45 | 5.0 | 2.6 | rectangular |
| Comparative Example | 8 | 24 | 50 | 55 | 6.5 | 3.6 | rectangular |
| | 9 | 24 | 50 | 55 | 6.2 | 3.5 | rectangular |
| | 10 | 24 | 50 | 55 | 5.6 | 3.6 | rectangular |
| | 11 | 25 | 50 | 55 | 5.7 | 3.6 | rectangular |

IS: Isolated space:

Examples 67 to 69 and Comparative Examples 12, 13

EUV Exposure Test 2

Each of the negative resist compositions (prepared above as Examples 67 to 69 and Comparative Examples 12, 13) was spin coated on a silicon substrate (diameter 4 inches, vapor primed with HMDS) and prebaked on a hot plate at 105° C. for 60 seconds to form a resist film of 50 nm thick. EUV exposure was performed by dipole illumination at NA 0.3. Immediately after the exposure, the resist film was baked (PEB) on a hot plate for 60 seconds and puddle developed in a 2.38 wt % TMAH aqueous solution for 30 seconds to form a negative pattern.

The optimum exposure (Eop) is defined as the exposure dose that provides a 1:1 resolution of a 35-nm line-and-space pattern. Maximum resolution is a minimum size that can be resolved at Eop. The 35-nm LS pattern was measured for LER under SEM. On observation in cross section of the resist pattern under SEM, it was visually judged whether or not the pattern profile was rectangular.

The results of the resist compositions by EUV lithography test are shown in Table 16.

TABLE 16

| | Eop (LS), $mJ/cm^2$ | Maximum resolution (LS), nm | LER, nm | Pattern profile |
|---|---|---|---|---|
| Example 67 | 26 | 28 | 4.7 | rectangular |
| Example 68 | 28 | 30 | 4.9 | rectangular |
| Example 69 | 26 | 30 | 4.8 | rectangular |
| Comparative Example 12 | 27 | 45 | 6.1 | rectangular |
| Comparative Example 13 | 26 | 45 | 5.9 | rectangular |

As seen from the results in Tables 15 and 16, the negative resist compositions containing the sulfonium salt of formula (1) within the scope of the invention (Examples 38 to 66 or Examples 67 to 69) exhibit a high resolution, satisfactory pattern rectangularity, and acceptable values of CDU and LER. In contrast, the resist compositions containing a sulfonium salt which is less bulky than the sulfonium salt of formula (1) (Comparative Examples 8 to 11 or Comparative Examples 12, 13) are inferior in resolution, CDU, and LER. This is because the sulfonium salts used in Comparative Examples are less bulky than the sulfonium salts of formula (1) and fail in effective control of acid diffusion.

It has been demonstrated that using the resist composition within the scope of the invention, a pattern having CDU and minimal LER can be formed via exposure. The pattern forming process using the resist composition within the scope of the invention is advantageous in the photolithography for semiconductor device fabrication and photomask blank processing.

While the invention has been illustrated and described in typical embodiments, it is not intended to be limited to the details shown. Any modified embodiments having substantially the same features and achieving substantially the same results as the technical idea disclosed herein are within the spirit and scope of the invention.

Japanese Patent Application No. 2014-195029 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A resist composition comprising:
a sulfonium salt having the general formula (1):

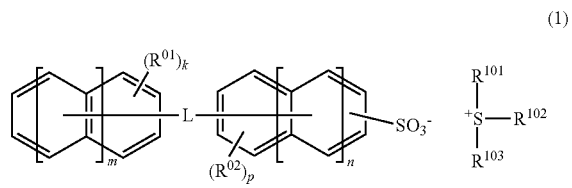

(1)

wherein $R^{01}$ is a $C_3$-$C_{20}$ branched or cyclic monovalent hydrocarbon group which may be substituted with or separated by a heteroatom,
m is an integer of 0 to 2, k is an integer satisfying $1 \leq k \leq 5+4m$,
$R^{101}$, $R^{102}$ and $R^{103}$ are each independently a $C_1$-$C_{20}$ straight or $C_3$-$C_{20}$ branched or cyclic monovalent hydrocarbon group which may be substituted with or separated by a heteroatom, or at least two of $R^{101}$, $R^{102}$ and $R^{103}$ may bond together to form a ring with the sulfur atom,
L is an ester, sulfonic acid ester, carbonate or carbamate bond,
$R^{02}$ is a $C_1$-$C_{10}$ straight or $C_3$-$C_{20}$ branched or cyclic monovalent hydrocarbon group which may be substituted with or separated by a heteroatom,
n is an integer of 0 to 2, and p is an integer satisfying $0 \leq p \leq 4+4n$; and
a polymer comprising recurring units having the general formula (U-1):

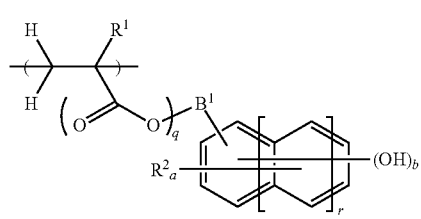

(U-1)

wherein q is 0 or 1, r is an integer of 0 to 2, $R^1$ is hydrogen, fluorine, methyl or trifluoromethyl, $R^2$ is each independently hydrogen or $C_1$-$C_6$ alkyl group, $B^1$ is a single bond or a $C_1$-$C_{10}$ alkylene group which may contain an ether bond, a is an integer satisfying $a \leq 5+2r-b$, and b is an integer of 1 to 3;

wherein the polymer further comprises recurring units having the general formula (U-3) and/or (U-4):

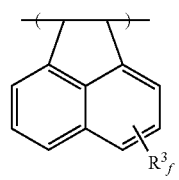

(U-3)

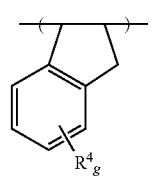

(U-4)

wherein f is an integer of 0 to 6, $R^3$ is each independently hydrogen, or a $C_1$-$C_6$ alkyl, primary or secondary alkoxy, or $C_1$-$C_7$ alkylcarbonyloxy group which may be substituted with halogen, g is an integer of 0 to 4, and $R^4$ is each independently hydrogen, or a $C_1$-$C_6$ alkyl, primary or secondary alkoxy, or $C_1$-$C_7$ alkylcarbonyloxy group which may be substituted with halogen.

2. The resist composition of claim 1 which is a chemically amplified positive tone resist composition, the polymer comprising recurring units adapted to be decomposed under the action of acid to increase the solubility in alkaline developer.

3. The resist composition of claim 2 wherein the recurring unit adapted to be decomposed under the action of acid to increase the solubility in alkaline developer has the general formula (U-2):

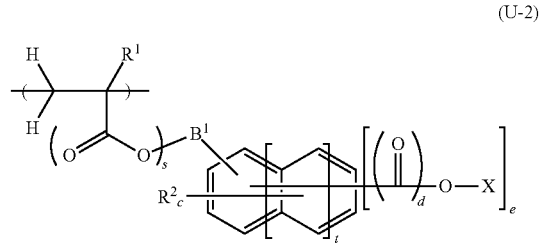

(U-2)

wherein s is 0 or 1, t is an integer of 0 to 2, $R^1$, $R^2$ and $B^1$ are as defined above, c is an integer satisfying $c \leq 5+2t-e$, d is 0 or 1, e is an integer of 1 to 3, X is an acid labile group when e=1, X is hydrogen or an acid labile group when e=2 or 3, with at least one Y being an acid labile group.

4. The resist composition of claim 1 which is a chemically amplified negative tone resist composition, the polymer comprising, in addition to the recurring units having formula (U-1), recurring units having the general formula (UN-2):

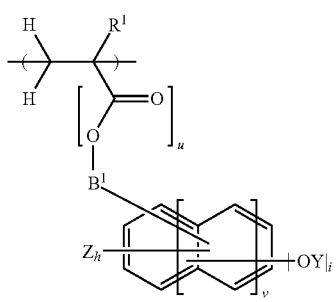
(UN-2)

wherein $R^1$ and $B^1$ are as defined above,

Z is hydrogen, or a $C_1$-$C_{20}$ straight, branched or cyclic alkyl, $C_2$-$C_{20}$ hydroxyalkyl, $C_2$-$C_{20}$ alkoxyalkyl, $C_2$-$C_{20}$ alkylthioalkyl, halogen, nitro, cyano, sulfinyl, or sulfonyl group, Y is a $C_1$-$C_{20}$ alkyl or $C_1$-$C_{20}$ acyl group, h is an integer of 0 to 4, i is an integer of 0 to 5, u is 0 or 1, and v is an integer of 0 to 2.

5. The resist composition of claim 4, further comprising a crosslinker.

6. The resist composition of claim 1 wherein the anion moiety in the sulfonium salt is selected from the group consisting of the following formulae:

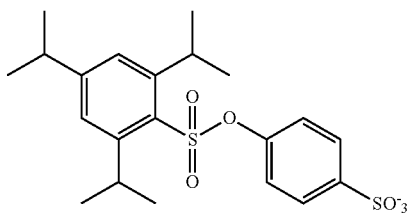

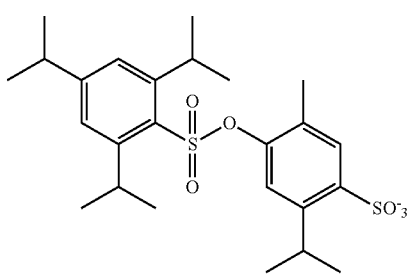

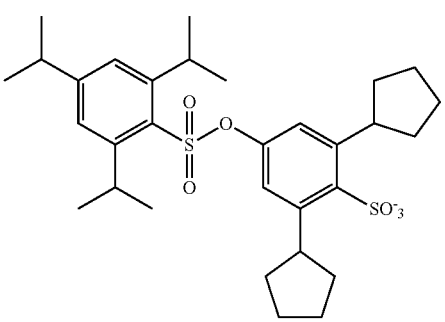

-continued

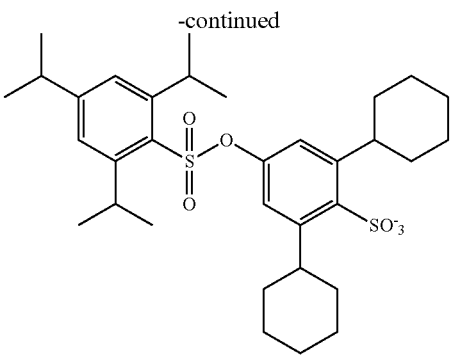

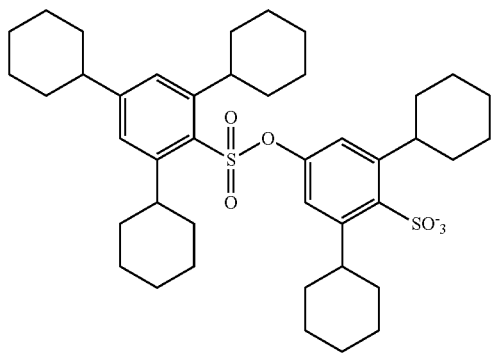

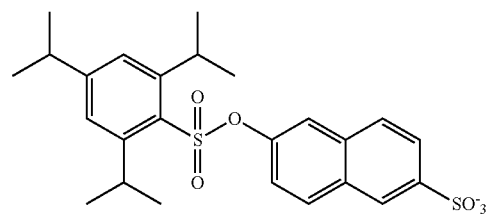

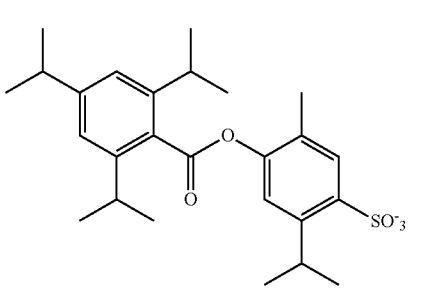

71
-continued
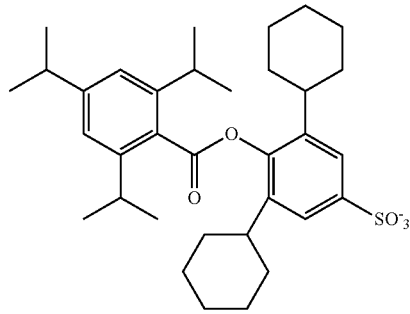
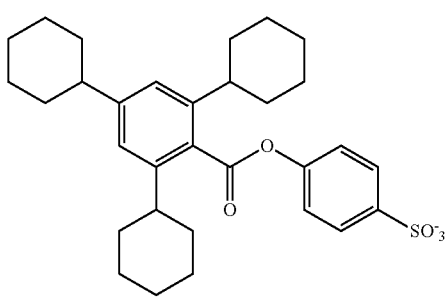
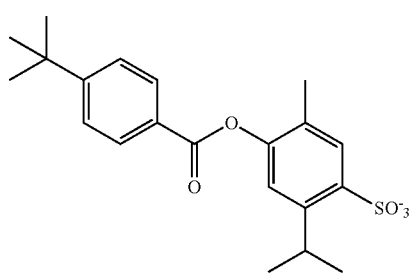
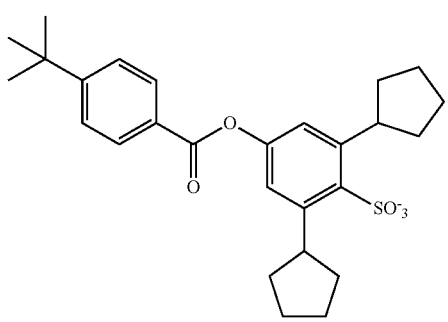
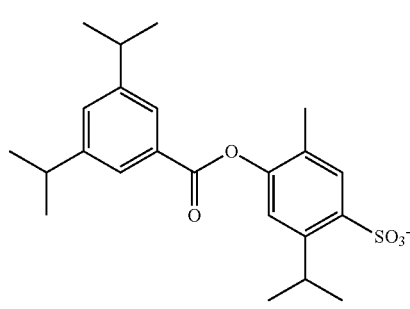
72
-continued
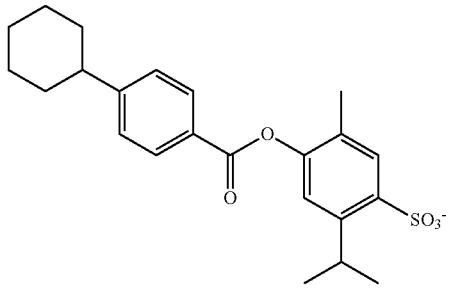
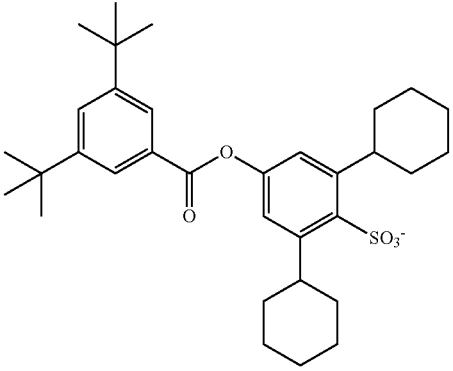
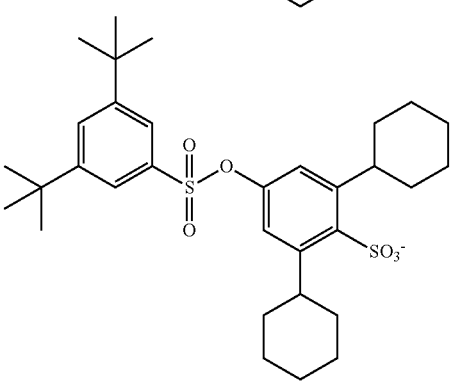
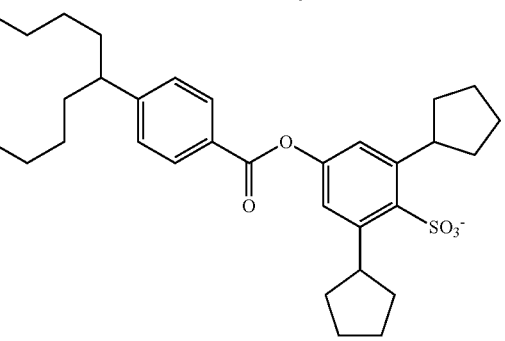
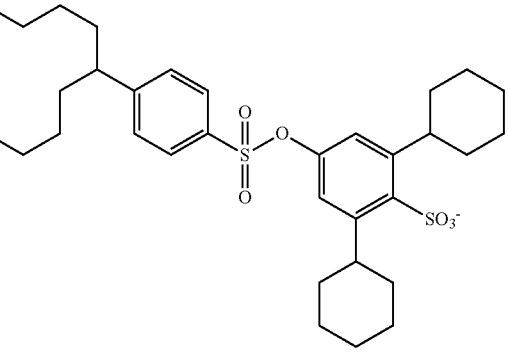

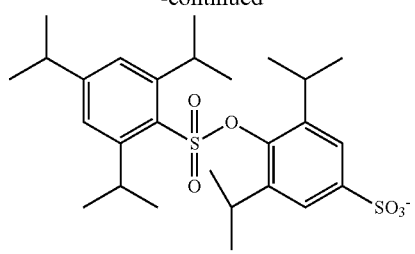
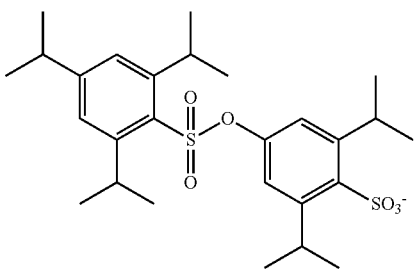
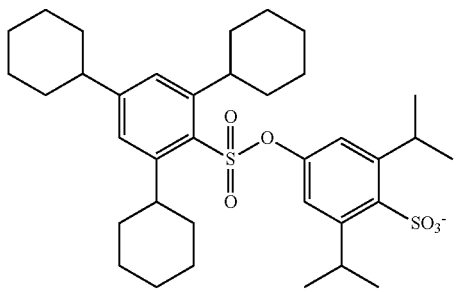
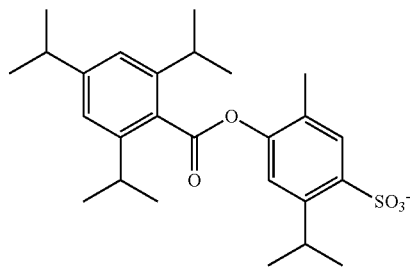
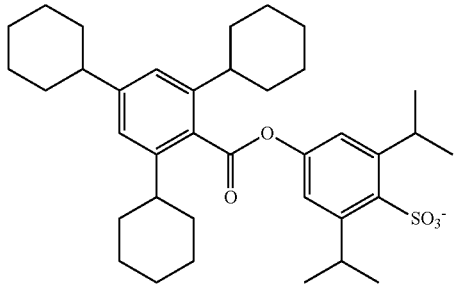
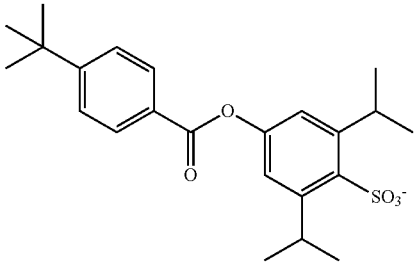

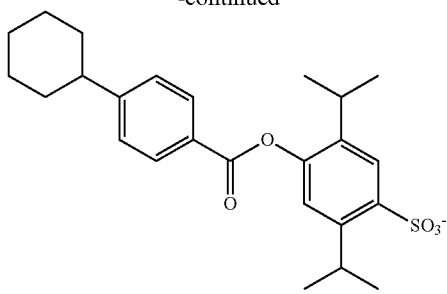
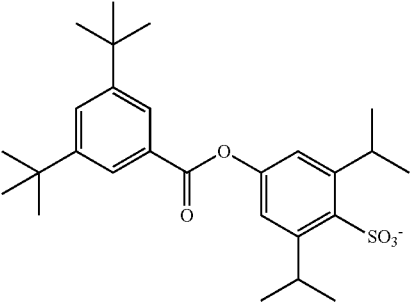
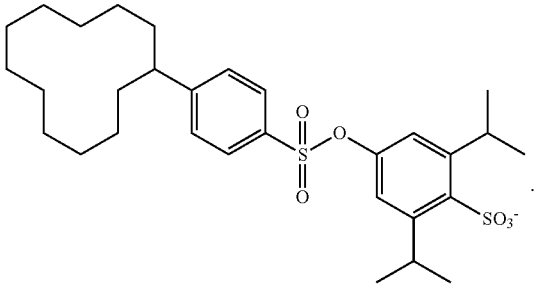

7. The resist composition of claim 1 wherein n is 0.
8. The resist composition of claim 1 wherein k is an integer of 1 to 3.
9. A resist composition comprising:
a sulfonium salt having the general formula (1):

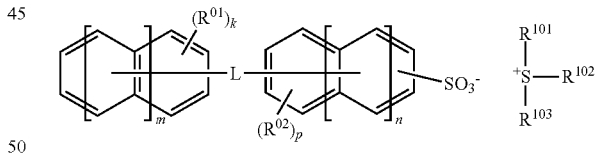

(1)

wherein $R^{01}$ is a $C_3$-$C_{20}$ branched or cyclic monovalent hydrocarbon group which may be substituted with or separated by a heteroatom,
m is an integer of 0 to 2, k is an integer satisfying $1 \leq k \leq 5+4m$,
$R^{101}$, $R^{102}$ and $R^{103}$ are each independently a $C_1$-$C_{20}$ straight or $C_3$-$C_{20}$ branched or cyclic monovalent hydrocarbon group which may be substituted with or separated by a heteroatom, or at least two of $R^{101}$, $R^{102}$ and $R^{103}$ may bond together to form a ring with the sulfur atom,
L is an ester, sulfonic acid ester, carbonate or carbamate bond,
$R^{02}$ is a $C_1$-$C_{10}$ straight or $C_3$-$C_{20}$ branched or cyclic monovalent hydrocarbon group which may be substituted with or separated by a heteroatom, n is an integer of 0 to 2, and p is an integer satisfying $0 \leq p \leq 4+4n$; and at least one of basic compounds having the general formulae (7) to (9):

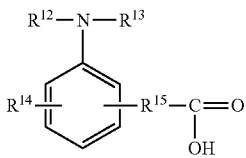
(7)

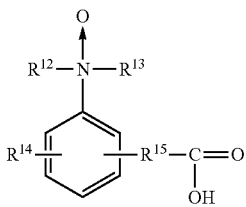
(8)

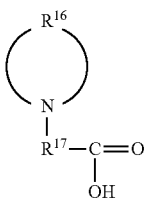
(9)

wherein $R^{12}$ and $R^{13}$ each are a $C_1$-$C_{20}$ straight, branched or cyclic alkyl, $C_6$-$C_{20}$ aryl, $C_7$-$C_{20}$ aralkyl, $C_2$-$C_{20}$ hydroxyalkyl, $C_2$-$C_{20}$ alkoxyalkyl, $C_2$-$C_{20}$ acyloxyalkyl, or $C_2$-$C_{20}$ alkylthioalkyl group, or $R^{12}$ and $R^{13}$ may bond together to form a cyclic structure with the nitrogen atom to which they are attached, $R^{14}$ is hydrogen, a $C_1$-$C_{20}$ straight, branched or cyclic alkyl, $C_6$-$C_{20}$ aryl, $C_7$-$C_{20}$ aralkyl, $C_2$-$C_{20}$ hydroxyalkyl, $C_2$-$C_{20}$ alkoxyalkyl, $C_2$-$C_{20}$ acyloxyalkyl, or $C_2$-$C_{20}$ alkylthioalkyl group, or halogen, $R^{15}$ is a single bond, a $C_1$-$C_{20}$ straight, branched or cyclic alkylene or $C_6$-$C_{20}$ arylene group, $R^{16}$ is an optionally substituted, $C_1$-$C_{20}$ straight or branched alkylene group which may contain at least one carbonyl, ether, ester or sulfide bond between two carbon atoms thereof, and $R^{17}$ is a $C_1$-$C_{20}$ straight, branched or cyclic alkylene or $C_6$-$C_{20}$ arylene group.

10. A pattern forming process comprising the steps of applying a resist composition onto a processable substrate to form a resist film, exposing patternwise the resist film to high-energy radiation, and developing in an alkaline developer to form a resist pattern;

wherein the resist composition comprises a sulfonium salt having the general formula (1):

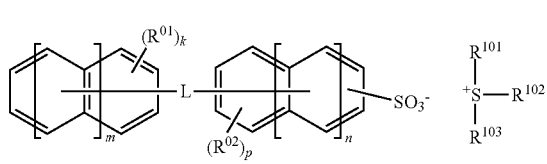
(1)

wherein $R^{01}$ is a $C_3$-$C_{20}$ branched or cyclic monovalent hydrocarbon group which may be substituted with or separated by a heteroatom, m is an integer of 0 to 2, k is an integer satisfying $1 \leq k \leq 5+4m$, $R^{101}$, $R^{102}$ and $R^{103}$ are each independently a $C_1$-$C_{20}$ straight or $C_3$-$C_{20}$ branched or cyclic monovalent hydrocarbon group which may be substituted with or separated by a heteroatom, or at least two of $R^{101}$, $R^{102}$ and $R^{103}$ may bond together to form a ring with the sulfur atom, L is an ester, sulfonic acid ester, carbonate or carbamate bond, $R^{02}$ is a $C_1$-$C_{10}$ straight or $C_3$-$C_{20}$ branched or cyclic monovalent hydrocarbon group which may be substituted with or separated by a heteroatom, n is an integer of 0 to 2, and p is an integer satisfying $0 \leq p \leq 4+4n$; and wherein the processable substrate has an outermost surface made of a chromium-containing material.

11. The process of claim 10 wherein the high-energy radiation is EUV or EB.

12. A pattern forming process comprising the steps of applying a resist composition onto a processable substrate to form a resist film, exposing patternwise the resist film to high-energy radiation, and developing in an alkaline developer to form a resist pattern;

wherein the resist composition comprises a sulfonium salt having the general formula (1):

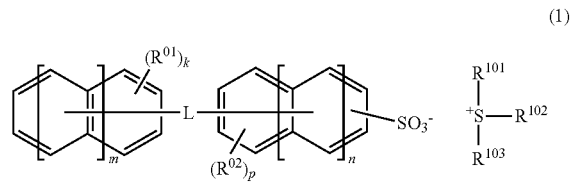
(1)

wherein $R^{01}$ is a $C_3$-$C_{20}$ branched or cyclic monovalent hydrocarbon group which may be substituted with or separated by a heteroatom, m is an integer of 0 to 2, k is an integer satisfying $1 \leq k \leq 5+4m$, $R^{101}$, $R^{102}$ and $R^{103}$ are each independently a $C_1$-$C_{20}$ straight or $C_3$-$C_{20}$ branched or cyclic monovalent hydrocarbon group which may be substituted with or separated by a heteroatom, or at least two of $R^{101}$, $R^{102}$ and $R^{103}$ may bond together to form a ring with the sulfur atom, L is an ester, sulfonic acid ester, carbonate or carbamate bond, $R^{02}$ is a $C_1$-$C_{10}$ straight or $C_3$-$C_{20}$ branched or cyclic monovalent hydrocarbon group which may be substituted with or separated by a heteroatom, n is an integer of 0 to 2, and p is an integer satisfying $0 \leq p \leq 4+4n$; and wherein the processable substrate is a photomask blank.

13. A sulfonium salt having the general formula (1):

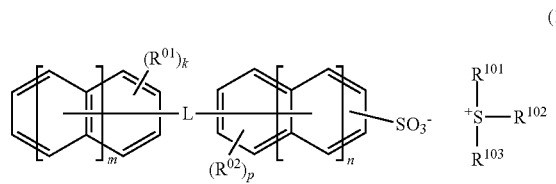

wherein $R^{01}$ is a $C_3$-$C_{20}$ branched or cyclic monovalent hydrocarbon group which may be substituted with or separated by a heteroatom, m is an integer of 0 to 2, k is an integer satisfying $1 \leq k \leq 5+4m$, $R^{101}$, $R^{102}$ and $R^{103}$ are each independently a $C_1$-$C_{20}$ straight or $C_3$-$C_{20}$ branched or cyclic monovalent hydrocarbon group which may be substituted with or separated by a heteroatom, or at least two of $R^{101}$, $R^{102}$ and $R^{103}$ may bond together to form a ring with the sulfur atom, L is an ester, sulfonic acid ester, carbonate or carbamate bond, $R^{02}$ is a $C_3$-$C_{20}$ branched or cyclic monovalent hydrocarbon group which may be substituted with or separated by a heteroatom, n is an integer of 0 to 2, and p is an integer satisfying $0 \leq p \leq 4+4n$.

14. A sulfonium salt having the general formula (1):

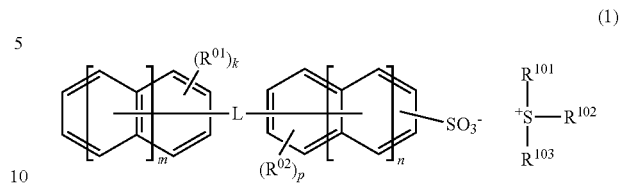

wherein $R^{01}$ is a $C_3$-$C_{20}$ branched or cyclic monovalent hydrocarbon group which may be substituted with or separated by a heteroatom, m is an integer of 0 to 2, k is an integer satisfying $1 \leq k \leq 5+4m$, $R^{101}$, $R^{102}$ and $R^{103}$ are each independently a $C_1$-$C_{20}$ straight or $C_3$-$C_{20}$ branched or cyclic monovalent hydrocarbon group which may be substituted with or separated by a heteroatom, or at least two of $R^{101}$, $R^{102}$ and $R^{103}$ may bond together to form a ring with the sulfur atom, L is an ester, sulfonic acid ester, carbonate or carbamate bond, $R^{02}$ is a $C_1$-$C_{10}$ straight or $C_3$-$C_{20}$ branched or cyclic monovalent hydrocarbon group which may be substituted with or separated by a heteroatom, n is an integer of 0 to 2, and p is 2 or 3.

* * * * *